(12) United States Patent
Hinz et al.

(10) Patent No.: US 10,487,357 B2
(45) Date of Patent: Nov. 26, 2019

(54) METHODS OF NUCLEIC ACID ANALYSIS USING TERMINATOR NUCLEOTIDES

(71) Applicants: Life Technologies Corporation, Carlsbad, CA (US); LIFE TECHNOLOGIES GmBH, Darmstadt (DE)

(72) Inventors: Wolfgang Hinz, Carlsbad, CA (US); Steven Menchen, Fremont, CA (US); Ronald Graham, Carlsbad, CA (US); Peter Vander Horn, Encinitas, CA (US); Earl Hubbell, Palo Alto, CA (US); Christian Woehler, Darmstadt (DE); Roman Rozhkov, Carlsbad, CA (US); Barnett Rosenblum, San Jose, CA (US)

(73) Assignees: Life Technologies Corporation, Carsbad, CA (US); Life Technologies GmbH, Darmstadt (DE)

( * ) Notice: Subject to any disclaimer, the term of this patent is extended or adjusted under 35 U.S.C. 154(b) by 0 days.

(21) Appl. No.: 15/561,445

(22) PCT Filed: Mar. 18, 2016

(86) PCT No.: PCT/US2016/023139
§ 371 (c)(1),
(2) Date: Sep. 25, 2017

(87) PCT Pub. No.: WO2016/153999
PCT Pub. Date: Sep. 29, 2016

(65) Prior Publication Data
US 2018/0119217 A1    May 3, 2018

Related U.S. Application Data

(63) Continuation-in-part of application No. 14/856,220, filed on Sep. 16, 2015.

(60) Provisional application No. 62/138,236, filed on Mar. 25, 2015.

(51) Int. Cl.
*C12P 19/34* (2006.01)
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

| | | | |
|---|---|---|---|
| 7,057,026 B2 | 6/2006 | Barnes et al. | |
| 7,566,537 B2 | 7/2009 | Balasubramanian et al. | |
| 7,635,578 B2 | 12/2009 | Ju et al. | |
| 7,713,698 B2 | 5/2010 | Ju et al. | |
| 7,785,796 B2 | 8/2010 | Balasubramanian et al. | |
| 7,790,869 B2 | 9/2010 | Ju et al. | |
| 7,883,869 B2 | 2/2011 | Ju et al. | |
| 7,888,015 B2* | 2/2011 | Toumazou | C12Q 1/6825 435/6.11 |
| 7,893,227 B2 | 2/2011 | Wu et al. | |
| 7,897,737 B2 | 3/2011 | Wu et al. | |
| 7,948,015 B2 | 5/2011 | Rothberg et al. | |
| 7,964,352 B2 | 6/2011 | Wu et al. | |
| 8,088,575 B2 | 1/2012 | Ju et al. | |
| 8,148,503 B2 | 4/2012 | Litosh et al. | |
| 8,158,346 B2 | 4/2012 | Balasubramanian et al. | |
| 8,198,029 B2 | 6/2012 | Wu et al. | |
| 8,361,727 B2 | 1/2013 | Wu et al. | |
| 8,497,360 B2 | 7/2013 | Litosh et al. | |
| 9,617,590 B2* | 4/2017 | Edwards | C12Q 1/6869 |
| 2003/0215862 A1* | 11/2003 | Parce | C12Q 1/6874 435/6.11 |
| 2008/0166727 A1 | 7/2008 | Esfandyarpour et al. | |
| 2009/0026082 A1 | 1/2009 | Rothberg et al. | |
| 2009/0127589 A1 | 5/2009 | Rothberg et al. | |
| 2009/0203531 A1 | 8/2009 | Kurn | |
| 2010/0137143 A1 | 6/2010 | Rothberg et al. | |
| 2010/0197507 A1 | 8/2010 | Rothberg et al. | |
| 2010/0282617 A1 | 11/2010 | Rothberg et al. | |

(Continued)

OTHER PUBLICATIONS

PCT/US2016/023139, International Search Report and Written Opinion dated Jun. 16, 2016, 11 pages.
Anderson, et al., "A system for multiplexed direct electrical detection of DNA synthesis", Sensors and Actuators B Chemical, vol. 129, No. 1, 2008, 79-86.
Pourmand et al., "Direct electrical detection of DNA synthesis", Proceedings of the National Academy of Sciences, vol. 103, No. 17, 2006, 6466-6470.
Purushothaman et al., "Towards Fast Solid State DNA Sequencing", IEEE ISCAS 2002 Proceedings, Circuits and Systems, vol. 4, 2002, pp. IV-169-IV-172.

(Continued)

*Primary Examiner* — Kenneth R Horlick
(74) *Attorney, Agent, or Firm* — Life Technologies Corporation; Paula Schoeneck

(57) ABSTRACT

In some embodiments, the disclosure relates generally to methods, as well as related, systems, compositions, kits and apparatuses, for nucleic acid analysis that involve the use of modified nucleotides, including terminator nucleotides and/or tagged nucleotides, in a template-dependent nucleotide incorporation reaction. In some embodiments, the nucleic acid analysis can be conducted at a single reaction site, or at a plurality of reaction sites in an array of reaction sites. Optionally, the array contains a plurality of reaction sites having about 1-100 million, or about 100-250 million, or about 200-500 million, or about 500-900 million, or more reaction sites. Optionally, each reaction site is in contact with, operatively coupled, or capacitively coupled to one or more sensors that are ion-sensitive FETs (isFETs) or chemically-sensitive FETs (chemFETs) sensors. Optionally, the reaction sites are in fluid communication with each other.

20 Claims, 5 Drawing Sheets
Specification includes a Sequence Listing.

(56) References Cited

U.S. PATENT DOCUMENTS

| | | |
|---|---|---|
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2012/0052489 A1 | 3/2012 | Gordon et al. |
| 2014/0242579 A1* | 8/2014 | Zhou ..................... C07H 19/10 435/6.11 |
| 2014/0329712 A1* | 11/2014 | Edwards .............. C12Q 1/6869 506/9 |
| 2016/0097091 A1 | 4/2016 | Hinz et al. |

OTHER PUBLICATIONS

Sakata et al., "DNA Sequencing Based on Intrinsic Molecular Charges", Angewandte Chemie International, vol. 118, 2006, pp. 2283-2286.

Sakurai et al., "Real-Time Monitoring of DNA Polymerase Reactions by a Micro ISFET pH Sensor", Analytical Chemistry, vol. 64, No. 17, 1992, pp. 1996-1997.

* cited by examiner $L_1$ = neutral cleavable linkage, $L_2$ = lipophilic group $L_2$ = anionic cleavable linkage, $L_2$ = hydrophilic group

SEQUENCE LISTING

```
<160> NUMBER OF SEQ ID NOS: 1

<210> SEQ ID NO 1
<211> LENGTH: 581
<212> TYPE: PRT
<213> ORGANISM: Bacillus stearothermophilus

<400> SEQUENCE: 1

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110
```

```
Asp Asp Val Ala Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
                340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
                420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
                500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
```

-continued

```
            530                 535                 540
Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580
```

METHODS OF NUCLEIC ACID ANALYSIS USING TERMINATOR NUCLEOTIDES

CROSS-REFERENCE TO RELATED APPLICATIONS

This application is a U.S. National Application filed under 35 U.S.C. § 371 of International Application No. PCT/US2016/023139, filed on Mar. 18, 2016, which claims the benefit of priority under 35 U.S.C. § 119 to U.S. Provisional Application No. 62/138,236, filed Mar. 25, 2015; and International Application No. PCT/US2016/023139, is a Continuation-in-Part of U.S. Non-Provisional application Ser. No. 14/856,220, filed Sep. 16, 2015, the disclosures of all of the aforementioned applications are incorporated by reference in their entireties.

Throughout this application various publications, patents, and/or patent applications are referenced. The disclosures of these publications, patents, and/or patent applications in their entireties are hereby incorporated by reference into this application in order to more fully describe the state of the art to which this invention pertains.

SUMMARY

In some embodiments, the disclosure relates generally to methods (and related compositions, systems, apparatuses and kits) for nucleic acid sequencing, comprising: (a) providing a surface including one or more reaction sites containing a polymerase and a nucleic acid template hybridized to an extendible end; (b) performing a first nucleotide flow by contacting one or more of the reaction sites with a first solution including one or more types of terminator nucleotide; (c) incorporating at least one type of terminator nucleotide at the extendible end of the nucleic acid template contained within at least one of the reaction sites using the polymerase; and (d) detecting a signal (e.g., a non-optical signal) indicating the nucleotide incorporation using a sensor that is attached or operatively linked to the at least one reaction site.

In some embodiments, the terminator nucleotide includes a terminator moiety. In some embodiments, the terminator nucleotide comprises a ribose or deoxyribose having a terminator moiety linked to the 2' or 3' or 4' position of the ribose or deoxyribose.

In some embodiments, the terminator moiety comprises a carbonyl, carbonate, carbamate moiety.

In some embodiments, the terminator moiety comprises a disulfide group.

In some embodiments, the method further comprises analyzing the non-optical signal.

In some embodiments, the methods further comprise identifying the incorporated terminator nucleotide.

In some embodiments, the methods further comprise deblocking the terminator nucleotide.

Optionally, the deblocking includes removing the terminator moiety from the terminator nucleotide.

Optionally, the terminator group that can be removed or cleaved with a cleaving agent.

Optionally, the cleaving agent includes an enzyme, a chemical compound, acidic or basic conditions, heat, or light.

In some embodiments, the method further comprises performing a second nucleotide flow by contacting at least some of the reaction sites with a second solution containing one or more types of nucleotide.

Optionally, the first and/or the second solutions include only a single type of nucleotide.

Optionally, the first solution includes a terminator nucleotide, non-terminator nucleotide or both terminator and non-terminator nucleotides.

Optionally, the second solution includes a terminator nucleotide, non-terminator nucleotide or both terminator and non-terminator nucleotides.

In some embodiments, the methods comprise performing a first nucleotide flow which includes a first series of nucleotide flows. The first series of nucleotide flows include a plurality of nucleotide flows, each nucleotide flow in the first series including contacting one or more of the reaction sites with a solution including one or more nucleotide types.

In some embodiments, after each nucleotide flow in the first series and prior to the next flow, the method includes detecting nucleotide incorporation (or lack thereof) occurring at the one or more reaction sites.

In some embodiments, the method further comprises determining the identity and number of nucleotides incorporated following each nucleotide flow in the first series.

In some embodiments, the methods comprise performing a second nucleotide flow which includes a second series of nucleotide flows. The second series of nucleotide flows include a plurality of nucleotide flows, each nucleotide flow in the second series including contacting one or more of the reaction sites with a solution including one or more nucleotide types.

In some embodiments, after each nucleotide flow in the second series and prior to the next flow, the method includes detecting nucleotide incorporation (or lack thereof) occurring at the one or more reaction sites.

In some embodiments, the method further comprises determining the identity and number of nucleotides incorporated following each nucleotide flow in the second series.

In some embodiments, the method further comprises denaturing or removing the extendible end from the nucleic acid template after completing the first series and prior to commencing the second series.

Optionally the first series of nucleotide flows includes at least one flow containing a terminator nucleotide, or a non-terminator nucleotide, or both a terminator nucleotide and a non-terminator nucleotide.

Optionally, the second series of nucleotide flows includes at least one flow containing a containing a terminator nucleotide, or a non-terminator nucleotide, or both a terminator nucleotide and a non-terminator nucleotide.

Optionally, the first series of nucleotide flows consists only of flows containing a terminator nucleotide.

Optionally, the second series of nucleotide flows consists only of flows containing a terminator nucleotide.

Optionally, the first series of nucleotide flows consists only of flows containing a non-terminator nucleotide.

Optionally, the second series of nucleotide flows consists only of flows containing a non-terminator nucleotide.

Optionally, the first series of nucleotide flows includes at least one flow containing a non-terminator nucleotide.

Optionally, the second series of nucleotide flows includes at least one flow containing a non-terminator nucleotide.

Optionally, the first series of nucleotide flows includes at least one flow containing a terminator nucleotide.

Optionally, the second series of nucleotide flows includes at least one flow containing terminator nucleotide.

Optionally, the first series consists only of flows containing a terminator nucleotide and the second series consists only of flows containing a non-terminator nucleotide.

Optionally, the first series consists only of flows containing a non-terminator nucleotide and the second series consists only of flows containing a terminator nucleotide.

In some embodiments, the method further comprises identifying the nucleotide with an error rate of less than 0.1%, or an error rate of less than 0.001%.

In some embodiments, the surface contains a plurality of reaction sites, each site having one or more sensors. For example, the surface contains about 1-100 million, or about 100-250 million, or about 200-500 million, or about 500-900 million, or more reaction sites, where each reaction site is in contact with, operatively coupled, or capacitively coupled to one or more sensors that are ion-sensitive FETs (isFETs) or chemically-sensitive FETs (chemFETs) sensors.

Optionally, the reaction sites are in fluid communication with each other.

Optionally, each reaction site, in the plurality of reaction sites, contains a nucleotide incorporation reaction that generates a nucleotide incorporation product, where the product is detected by the one or more isFET or chemFET sensors at each reaction site (e.g., in a massively parallel manner).

Optionally, about 100 million, or about 250 million, or about 500 million, or about 900 million reaction sites are separately detecting a nucleotide incorporation byproduct generated in each of the these reaction site, where the product is detected by the one or more isFET or chemFET sensors at each reaction site.

In some embodiments, the non-optical signal that is detected in step (d) comprises a change in concentration of a byproduct of nucleotide incorporation, including a change in the concentration of hydrogen ions (protons), phosphate anions, pyrophosphate anions, higher-order polyphosphate anions, and other suitable entities.

DETAILED DESCRIPTION

Figure 1:
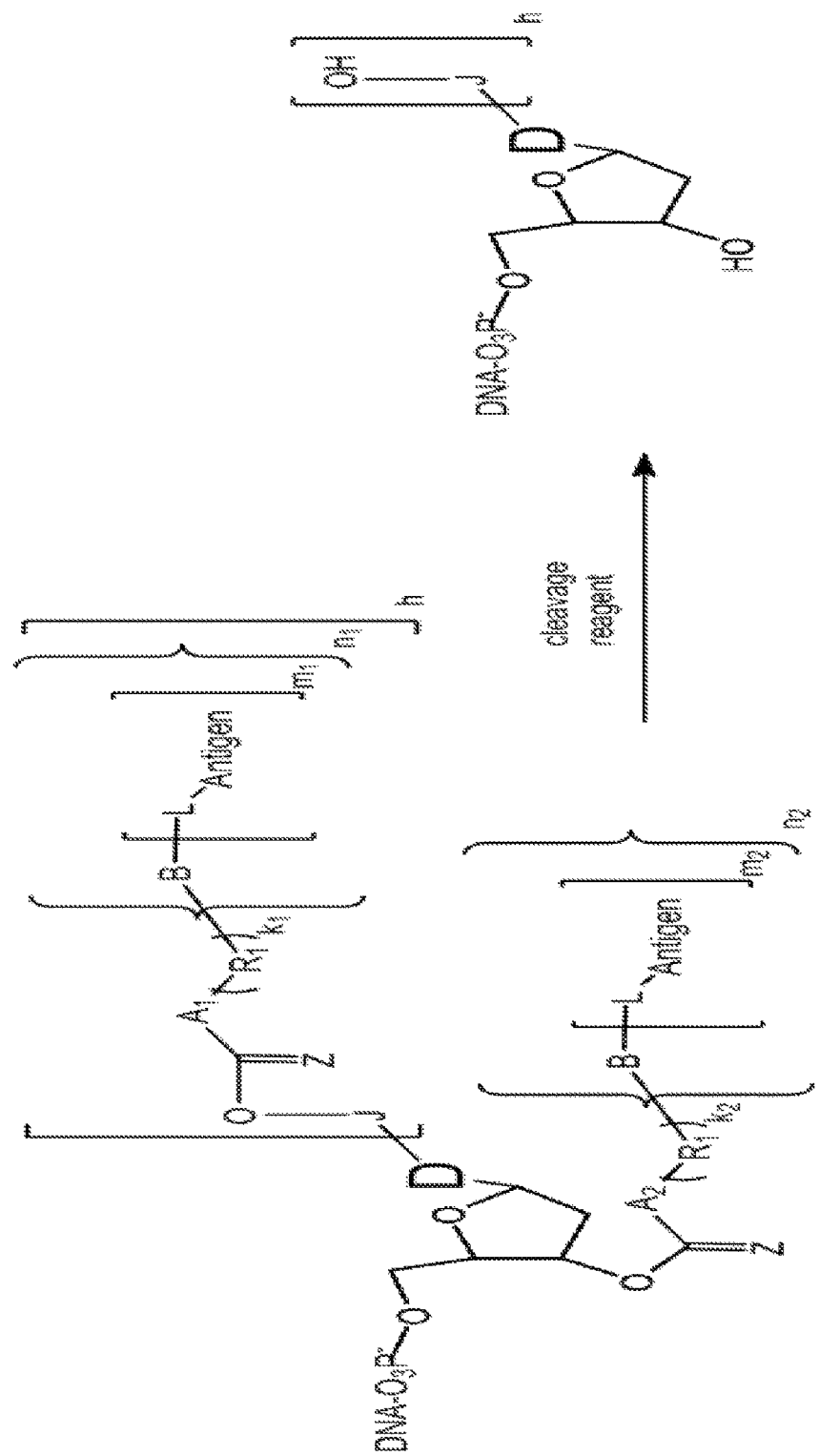
FIG. 1 shows several non-limiting examples of modified nucleotides.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In some embodiments, the disclosure relates generally to compositions, as well as related, systems, methods, kits and apparatuses, for nucleotides. In some embodiments, the nucleotides comprise modified nucleotides.

As used herein, the term "nucleotide" and its variants refer to any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally-occurring nucleotides but also any modified nucleotides or derivatives that, regardless of their structure, can bind selectively to and can optionally be polymerized by, a polymerase. While naturally-occurring nucleotides typically comprise sugar, base, and phosphate moieties, the modified nucleotides can include compounds lacking any one, some or all of such moieties, or can include one or more substitute groups.

In some embodiments, the disclosure relates generally to compositions, as well as related, systems, methods, kits and apparatuses, for modified nucleotides that include ribonucleotides, deoxyribonucleotides, ribonucleotide polyphosphate molecules, deoxyribonucleotide polyphosphate molecules, peptide nucleotides, nucleoside polyphosphate molecules, metallonucleosides, phosphonate nucleosides, and modified phosphate-sugar backbone nucleotides, and any analogs or variants of the foregoing.

In some embodiments, the disclosure relates generally to compositions, as well as related, systems, methods, kits and apparatuses, for modified nucleotides that are reversible terminator nucleotides and non-reversible terminator nucleotides.

In some embodiments, the disclosure relates generally to compositions, as well as related, systems, methods, kits and apparatuses, for terminator nucleotides that can be incorporated into an extendible end of a nucleic acid molecule, and optionally in a template-dependent manner by a polymerase. In some embodiments, the terminator nucleotide will, once incorporated, inhibit or block further nucleotide incorporations at the end of the nucleic acid molecule. The incorporation of the terminator nucleotide can convert the extendible end into a non-extendible end. Optionally, the terminator nucleotide includes a terminator group (also referred to as a terminator moiety or a blocking moiety or blocking group) that confers the ability to inhibit or block further nucleotide incorporations. In some embodiments, the terminator nucleotides can be operably linked to at least one terminator group or moiety. In some embodiments, at least one terminator group can be operably linked to any portion of the base, sugar, phosphate group or any phosphate in the phosphate chain. In some embodiments, the terminator group can be neutralized, cleaved, or otherwise removed from the terminator nucleotide via suitable treatments. In some embodiments, neutralization, cleavage or removal of the terminator group can permit subsequent nucleotide incorporations to occur. In some embodiments, the non-extendible end can be converted to an extendible end via cleavage, neutralization or removal of the terminator group. In some embodiments, the terminator group cannot be neutralized, cleaved, or otherwise removed from the terminator nucleotide via suitable treatments (e.g., non-reversible terminator nucleotides).

In some embodiments, the disclosure relates generally to compositions, as well as related, systems, methods, kits and apparatuses, for modified nucleotides that are operably linked to one or more tags. In some embodiments, the tags include a label. In some embodiments, the modified nucleotides are un-tagged nucleotides.

In some embodiments, the disclosure relates generally to compositions, as well as related, systems, methods, kits and apparatuses, for modified nucleotides that are incorporatable or non-incorporatable nucleotides.

In some embodiments, the disclosure relates generally to compositions, as well as related, systems, methods, kits and apparatuses, for modified nucleotides that comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124.; and U.S. Pat. No. 5,558,991; these reference are expressly incorporated herein by reference as if set forth in full).

In some embodiments, the disclosure relates generally to compositions, as well as related, systems, methods, kits and apparatuses, for modified nucleotides that comprise a base moiety. The base moiety can include substituted or unsubstituted nitrogen-containing parent heteroaromatic ring which is commonly found in nucleic acids, including naturally-occurring, substituted, modified, engineered variants, analog or modified nucleotides. In some embodiments, the modified nucleotides include a base that is a non-naturally occurring base. Typically, the base is capable of undergoing base pairing with another base according to a predetermined paradigm. For example, in some embodiments, the base is capable of forming Watson-Crick and/or Hoogstein hydrogen bonds with an appropriate complementary base. Alternatively, the base can be capable of base pairing according to a set of preestablished rules that do not include Watson-Crick pairings. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

In some embodiments, the disclosure relates generally to compositions, as well as related, systems, methods, kits and apparatuses, for modified nucleotides that optionally include one phosphate group or a chain of phosphorus atoms. The chain can include two, three, four, five, six, seven, eight, nine, ten or more phosphorus atoms. In some embodiments, the phosphorus chain can be attached to any carbon of a sugar ring, such as the 2', 3' or 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. At least one phosphorus atom can be part of a phosphate group. In the phosphorus chain, a phosphorus atom with a side group other than O can be a substituted phosphate group. Some examples of modified nucleotides having more than three phosphorus groups are described in Xu, U.S. Pat. No. 7,405,281, which are expressly incorporated herein by reference as if set forth in full. The phosphate groups include analogs, such as phosphoramidate, phosphorothioate, phosphorodithioate, and O-methylphosphoroamidite groups. At least one of the phosphate groups can be substituted with a fluoro and/or chloro group. The phosphate groups can be linked to the sugar moiety by an ester or phosphoramide linkage.

In some embodiments, the disclosure relates generally to compositions, as well as related, systems, methods, kits and apparatuses, for a modified nucleotide comprising a nucleotide linked to at least one terminator group which replaces a hydroxyl group at the 3' carbon position of the ribose deoxyribose (e.g., terminator nucleotide).

In some embodiments, the disclosure relates generally to compositions, as well as related, systems, methods, kits and apparatuses, for a modified nucleotide comprising a nucleotide linked to at least one tag group which replaces a hydroxyl group at the 3' carbon position of the ribose deoxyribose (e.g., tagged nucleotide).

In some embodiments, the disclosure relates generally to compositions, as well as related, systems, methods, kits and apparatuses, for a modified nucleotide comprising at least one terminator group that replaces the H at the 2' carbon position of a deoxyribose, or a terminator group that replaces an OH group at the 2' carbon position of a ribose (e.g., terminator nucleotide).

In some embodiments, the disclosure relates generally to compositions, as well as related, systems, methods, kits and apparatuses, for a modified nucleotide comprising at least one tag group that replaces the H at the 2' carbon position of a deoxyribose, or a tag group that replaces an OH group at the 2' carbon position of a ribose (e.g., tagged nucleotide).

In some embodiments, the disclosure relates generally to compositions, as well as related, systems, methods, kits and apparatuses, for a modified nucleotide comprising at least one terminator group that is placed at the 4' carbon position of a ribose or deoxyribose (e.g., terminator nucleotide).

In some embodiments, the disclosure relates generally to compositions, as well as related, systems, methods, kits and apparatuses, for a modified nucleotide comprising at least one tag group that is placed at the 4' carbon position of a ribose or deoxyribose (e.g., tagged nucleotide).

In some embodiments, the disclosure relates generally to compositions, as well as related, systems, methods, kits and apparatuses, for a modified nucleotide comprising at least one terminator group linked to any position of a purine or pyrimidine base, or any positions of analogs of purine or pyrimidine bases (e.g., terminator nucleotide).

In some embodiments, the disclosure relates generally to compositions, as well as related, systems, methods, kits and apparatuses, for a modified nucleotide comprising one or more tag groups linked to any position of a purine or pyrimidine base, or any positions of analogs of purine or pyrimidine bases (e.g., tagged nucleotides). In some embodiments, the nucleotides are tagged or un-tagged.

Optionally, the terminator or tag group can be linked to the N7 or O6 positions of a purine, or C5 position of a pyrimidine. Optionally, the terminator or tag group is linked to the NH group or C4 of a cytosine base, or linked to the O group or C4 of a uracil or thymine base, or linked to the N7 of a purine base. Optionally, the terminator or tag group is linked to the 7-position of a purine or deazapurine, or the N-6 position of a modified adenosine or N-2 position of a modified guanine. Optionally, the terminator or tag group is linked to the 5 position of a pyrimidine, such as cytidine, thymidine or uracil, or the N-4 position of a cytosine. For example, a 7-deazapurine base can be linked at the 7-position to a terminator group or tag group.

In some embodiments, the disclosure relates generally to compositions, as well as related, systems, methods, kits and apparatuses, for a modified nucleotide comprising a tagged or un-tagged nucleotide. In some embodiments, the disclosure relates generally to compositions, as well as related, systems, methods, kits and apparatuses, for a terminator nucleotide that is tagged or un-tagged. The term "tag group" also includes "tag moiety". In some embodiments, the tag comprises a label. In some embodiments, the tag is linked to any portion of the base, sugar or phosphate group or any phosphate in the phosphate chain. In some embodiments, the tag comprises a label that is a detectable label which produces, or causes to produce, fluorescence, luminescence, light, color, heat, or a chemical compound that is detectable. Optionally, the label is an affinity moiety.

In some embodiments, the tag is an optically-detectable label, a chemically-detectable or a non-optically detectable label (referred to herein as a non-optical label). In some embodiments, the optically detectable label includes a fluorescent or luminescent group. Optionally, the optically-detectable label comprises an energy transfer donor or acceptor fluorphore. The non-optical label can include a molecule, a chemical moiety, a compound, a radioisotope, a Raman label, an NMR label, a polynucleotide, an oligonucleotide, a protein, an antibody, a member of a binding pair (e.g., a biotin/avidin binding pair), an enzyme, an enzyme substrate, and the like.

In some embodiments, the modified nucleotide is linked to a tag group which comprises a charged group or is capable of becoming a charged group, or exhibits hyrdrophobicity or hydrophilicity properties, or sterically inhibits a polymerase from binding a subsequent nucleotide.

In some embodiments, the disclosure relates generally to compositions, as well as related, systems, methods, kits and apparatuses, for a modified nucleotide comprising a nucleotide operably linked to at least one terminator group and/or at least one tag group.

In some embodiments, the terminator group and/or tag group is larger than an H or OH group, is a charged group or is capable of being a charged group, exhibits hydrophobicity or hydrophilicity properties, sterically inhibits a polymerase from binding a subsequent nucleotide, or produces causes to be produced a detectable signal.

In some embodiments, the terminator group and/or the tag group comprises an allyl, alkyl, substitute alkyl, arylalkyl, alkenyl, alkynyl, aryl, heteroaryl, acyl, cyano, alkoxy, aryloxy, or heteroaryloxy moiety. In some embodiments, the modified nucleotides can include a 3' O allyl terminator group (U.S. Pat. Nos. 8,796,432 and 7,883,869, which are expressly incorporated herein by reference as if set forth in full). In some embodiments, the terminator group and/or the tag group comprises an amido, amine, aminoxy, or oxime moiety (e.g., aldoxime or ketoxime). In some embodiments, the terminator group and/or the tag group comprises an ether or ester moiety. In some embodiments, the terminator group and/or the tag group comprises a carbonyl, carbonate or carbamate moiety. In some embodiments, the terminator group and/or the tag group comprises a disulfide moiety. In some embodiments, the terminator group and/or the tag group comprises an electron drawing group. In some embodiments, the terminator group and/or the tag group comprises an azide or azidomethyl moiety. In some embodiments, the terminator group and/or the tag group comprises a phosphate moiety. In some embodiments, the terminator group and/or the tag group comprises a methyl, methylene or substituted methylene moiety. In some embodiments, the terminator group and/or the tag group comprises a heterocyclic moiety, optionally having a three-, four-, five- or six-sided ring structure. In some embodiments, the terminator group and/or the tag group comprises an amino acid or derivative thereof, including lysine or arginine. In some embodiments, the terminator group and/or the tag group comprises a neutral cleavable linkage group (e.g., lipophilic group). In some embodiments, the terminator group and/or the tag group comprises an anionic cleavable linker (e.g., hydrophilic). In some embodiments, the terminator group and/or the tag group comprises a neutral cleavable linker group and an anionic cleavable group. In some embodiments, the terminator group and/or the tag group comprises —O, —S, —P, —F, —NH$_2$, —OCH$_3$, —N$_3$, —OPO$_3$, —NHCOCH$_3$, 2-nitrobenzene carbonate, 2,4-dinitrobenzene sulfenyl, or tetrahydrofuranyl ether. See for example PCT publication Nos. WO 1991/06678 Tsien, and WO 2000/053805 Stemple, which are expressly incorporated by reference as if set forth in full. In some embodiments, the terminator group and/or the tag group comprises an affinity moiety, for example a biotin moiety.

In some embodiments, the terminator group and/or the tag group includes a linker. In some embodiments, the terminator group includes a linker and a moiety which blocks or inhibits incorporation of a subsequent nucleotide on an extending end of a nucleic acid. In some embodiments, the tag group includes a linker and a moiety that comprises a label that which produces, or causes to produce, fluorescence, luminescence, light, color, heat, or a chemical compound that is detectable. Optionally, the label is an affinity moiety.

In some embodiments, the disclosure relates generally to compositions, as well as related, systems, methods, kits and apparatuses, for a modified nucleotide comprising a nucleotide operably linked to at least one tag group which is a label that comprises a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. Optionally, the two reporter moieties include an energy transfer donor moiety and energy transfer acceptor moiety. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the disclosure relates generally to compositions, as well as related, systems, methods, kits and apparatuses, for a modified nucleotide comprising a nucleotide operably linked to at least one tag group which comprises at least one member of a binding partner. In some embodiments, a binding partners includes two molecules, or portions thereof, which have a specific binding affinity for one another and typically will bind to each other in preference to binding to other molecules. In some embodiments, binding partners include an "affinity moiety" and a "receptor moiety". Typically but not necessarily some or all of the structure of one member of a specific binding pair is complementary to some or all of the structure possessed by the other member, with the two members being able to bind together specifically by way of a bond between the complementary structures, optionally by virtue of multiple non-covalent attractions.

In some embodiments, molecules that function as binding partners include: biotin (and its derivatives) and its binding partners avidin, streptavidin and their derivatives; His-tags which bind nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

In some embodiments, an avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

In some embodiments, the disclosure relates generally to compositions, as well as related, systems, methods, kits and apparatuses, for a modified nucleotide comprising a nucleotide linked to a terminator group that can be removed or cleaved with a cleaving agent. In some embodiments, the cleaving agent includes an enzyme, a chemical compound, acidic or basic conditions, heat, or light. In some embodiments, the terminator moiety is not removable or cleavable.

In some embodiments, the disclosure relates generally to compositions, as well as related, systems, methods, kits and apparatuses, for a modified nucleotide comprising a nucleotide linked at the base to a tag group that can be removed or cleaved with a cleaving agent. In some embodiments, the cleaving agent includes an enzyme, a chemical compound, acidic or basic conditions, heat, or light. In some embodiments, the tag moiety is not removable.

In some embodiments, where the terminator nucleotide includes a terminator group linked to the 3' carbon position of the ribose or deoxyribose, cleavage or removal of the terminator group restores the 3'OH group at the 3' carbon position.

In some embodiments, where the terminator nucleotide includes a terminator group linked to the 2' carbon position of the ribose or deoxyribose, cleavage or removal of the terminator group restores the 2' H group of the deoxyribose or restores the 2'OH group of the ribose.

In some embodiments, where the modified nucleotide includes a tag linked to any position of the base, cleavage of the tag can remove a first portion of the tag and a second portion of the tag remains linked to the base (e.g., a scar).

In some embodiments, cleavage or removal of the terminator group is conducted with a single cleaving agent, or with two or more cleaving agents. For example, in a first cleaving event, at least a portion of a tag linked to a base is cleaved with a first cleaving agent, and in a second cleaving event the terminator group linked to the ribose or deoxyribose is cleaved with a second cleaving agent. In another example, a first cleaving agent removes a first portion of a tag that is linked to a base, and a second cleaving agent removes another portion of the tag from the base. In another example, a first cleaving agent removes a first portion of a terminator group that is linked to a ribose or deoxyribose, and a second cleaving agent removes another portion of the terminator group from the ribose or deoxyribose. Optionally, the first and the second cleaving event are sequential cleaving events, or the first and second cleaving events are conducted in the presence of both the first and second cleaving agents.

In some embodiments, the cleaving agent generates reductive or non-reductive hydrolysis.

In some embodiments, the cleaving agent is a chemical compound that causes the pH of the cleaving reaction to become basic or acidic. For example, the cleaving agent causes the pH to increase to about 7 to 9.5. In another example, the cleaving agent causes the pH to decrease to about 1.5 to 7.

Optionally, the cleaving agent comprises an enzyme that cleaves a peptide or peptide bonds, where the cleaving agent comprises a protease or trypsin.

Optionally, the cleaving agent comprises an enzyme that cleaves a lipid, where the cleaving agent comprises an esterase or lipase.

Optionally, the cleaving agent comprises an enzyme that cleaves a phosphate moiety or a moiety having a phosphorus atom, where the cleaving agent comprises a phosphatase.

Optionally, the cleaving agent comprises a transition metal that can form a metal-allyl complex. For example, the transition metals include platinum, palladium, rhodium, ruthenium, osmium and iridium.

Optionally, the cleaving agent comprises a fluoride ion, silver ion or mercury ion Optionally, the cleaving agent comprises silver fluoride, sodium fluoride, potassium fluoride, or tetraethyl ammonium fluoride.

Optionally, the cleaving agent comprises a phosphine compound, ammonia or hydroxide. Optionally, the phosphine compound comprises one or more sulfonate, amine, hydroxyl or carboxylate moiety. Optionally, the phosphine compound includes a derivatized tri-alkyl phosphine moiety. Optionally, the phosphine compound comprises tri-aryl phosphine moiety. Optionally, the phosphine compound comprises Tris(2-carboxyethyl)phosphine (also known as TCEP). Optionally, the phosphine compound comprises a bis-sulfo triphenyl phosphine (BS-TPP). Optionally, the cleaving agent comprises an aqueous solution having a phosphine compound. In some embodiments, the modified nucleotide comprises a 3' azido group (terminator moiety) which can be cleaved with a phosphine compound (U.S. Pat. No. 7,635,578, which are expressly incorporated herein by reference as if set forth in full).

In some embodiments, the modified nucleotides include a tag group linked to the NH group or C4 of a cytosine base, or linked to the O group or C4 of a uracil or thymine base, or linked to the N7 of a purine base. Optionally, the tag group is a benzyl moiety. Optionally, the alpha carbon of the benzyl moiety is substituted with one alkyl or aryl group. In some embodiments, the benzyl moiety can be functionalized to increase the terminator effects. In some embodiments, the benzyl moiety is non-cleavable. In some embodiments, the tag group can be linked to a fluorophore (dye) via a cleavable linker, which is optionally cleavable with a chemical, light, or enzyme. Optionally, the linker is cleavable with palladium compounds (e.g., sodium tetrachoropalladate (II), or palladium on activated carbon). See for example U.S. Pat. Nos. 7,893,227; 8,198,029; and 7,964,352, which are expressly incorporated herein by reference as if set forth in full.

In some embodiments, the modified nucleotides include a based linked to a tag group, where the tag group includes a 2-nitrobenzyl or nitrobenzyloxy moiety, or derivative thereof. Optionally, the modified nucleotides include a base linked to a detectable label (e.g., fluorophore) and terminator group, where the terminator group inhibits polymerase-mediated incorporation of a subsequent nucleotide. In some embodiments, the terminator group and/or label are attached to a linker which is optionally cleavable with a chemical, light, or enzyme. Optionally, the linker is cleavable with palladium compounds (e.g., sodium tetrachoropalladate (II), or palladium on activated carbon). See for example U.S. Pat. Nos. 8,497,360; 8,148,503; 7,897,737; and 8,361,727, which are expressly incorporated herein by reference as if set forth in full.

In some embodiments, the nucleotides are linked at the base with a detectable label. Optionally, the linker includes an allylic system. In some embodiments, the detectable labels includes a dye (e.g., optically-detectable dye), or a biotin-streptavidin system. In some embodiments, the detectable label acts as terminator group. Optionally, the detectable label can be linked to the 7-position of a purine or deazapurine, or the N-6 position of a modified adenosine or N-2 position of a modified guanine. Optionally, the detectable label can be linked to the 5 position of a pyrimidine, such as cytidine, thymidine or uracil, or the N-4 position of a cytosine. In some embodiments, the linkers include: a disulfide linkage, acid labile linkers (e.g., dialkoxybenzyl linkers), Sieber linkers, indole linkers, and t-butyl Sieber linkers. Optionally, the linkers are cleavable linkers, and include: electrophilically-cleavable linkers, nucleophilically-cleavable linkers, photocleavable linkers, and linkers cleavable under reductive or oxidative conditions. Optionally, the linkers are cleavable via use of safety-catch linkers, and linkers cleavable by elimination mechanisms. See for example U.S. Pat. No. 7,785,796, which is expressly incorporated herein by reference as if set forth in full. See also U.S. published application No. 2014/0106360, which is expressly incorporated herein by reference as if set forth in full.

In some embodiments, the nucleotides are linked at the base with a detectable label. For example, a 7-deazapurine base can be linked at the 7-position. Optionally, the linker attaching the base to the detectable label can be an acid labile linker, a photocleavable linker, disulfide linkage, dialkoxybenzyl linkers, Sieber linkers, indole linkers, or t-butyl Sieber linkers. Optionally, the linker that attaches the base to the detectable label can be cleavable under oxidation conditions, or cleavable with a palladium compound, or cleavable with thiophilic metals, including nickel, silver or mercury. In some embodiments, the terminator nucleotides also include a terminator group linked to the 2' or 3' sugar position by a linker. For example, the terminator group includes an azido group. In some embodiments, the linker attached to the base and the linker attached to the 2' or 3' sugar position are cleavable under the same conditions. See for example, U.S. Pat. Nos. 7,057,026; 7,566,537 and 8,158,346, which are expressly incorporated herein by reference as if set forth in full. Examples of other types of terminator nucleotides having 2' or 3' terminator groups are described in U.S. Pat. Nos. 7,541,444; 7,057,026; 7,592,435; 7,414,116; 7,427,673 and 8,399,188, and U.S. published application No. 2014/0249036, which are expressly incorporated herein by reference as if set forth in full.

In some embodiments, the nucleotides that are linked at the base with a detectable label. For example the linker comprises a photocleavable linker. Optionally, the cleavable linker comprises a nitrobenzyl moiety. In some embodiments, the terminator nucleotide can be linked at the 3' sugar position with a terminator group. Optionally, the terminator group comprises a small moiety. Exemplary small moieties include —$CH_2OCH_3$ (MOM) or —$CH_2CH$=$CH_2$ (allyl). See for example, U.S. Pat. Nos. 7,713,698; 7,790,869; 8,088,575; 7,635,578; and 7,883,869, which are expressly incorporated herein by reference as if set forth in full.

In some embodiments, the disclosure relates generally to methods, as well as related, systems, compositions, kits and apparatuses, for incorporating a modified nucleotide and detecting a signal which is associated with generating a nucleotide incorporation byproduct. As described herein, certain nucleic acid sequencing reactions involve the detection of nucleotide incorporation at the terminus of a nucleic acid strand. For example, certain sequencing reactions are based on the detection of the incorporation of a labeled nucleotide, wherein the label (e.g., a fluorescent moiety, a radionuclide) is incorporated as part of the nucleotide. In this manner, the presence and detection of the label as part of the immobilized nucleic acid strand can be indicative of nucleotide incorporation. In other examples, the label is released during incorporation of the nucleotide, and hence detection of the label in the mobile phase and/or effluent can be indicative of nucleotide incorporation. In certain example, exogenous labels are not necessary, as the natural byproducts of the nucleotide incorporation can be detected in the mobile phase and/or effluent. For example, such natural by-products include, but are not limited to, hydrogen ions (protons), phosphate anions, pyrophosphate anions, higher-order polyphosphate anions, and other suitable entities.

In some embodiments, it is desirable to improve methods and systems for detecting nucleotide incorporation events as described herein. For example, in some embodiments, where the nucleotide incorporation or by-products therefrom are detected as part of the sequencing workflow, such systems typically produce stoichiometric or sub-stoichiometric amounts of detectable products. As a consequence, the signal corresponding to this detection may be likewise no more than stoichiometric with respect to the incorporation event. As a result, the amount of signal capable of being detected for a given amount of nucleic acid incorporations may be limited. This issue may be of concern when the parameters of the sequencing method or systems are being decreased, such as by decreasing site size and/or increasing site density in substrates having a plurality of sites capable of detection. As the site size decreases, the amount of nucleic acid in each site, and consequently, the amount of signal produced, may decrease, thereby resulting in a lower signal. Such lower signals may reduce the signal to be detected for each incorporation event, as well as decrease the run length of the sequencing reaction, as signal tends to decrease with each sequential step. Therefore, it is desirable in certain embodiments to increase the magnitude and/or stoichiometric ratio between the nucleotide incorporation event or by-products therefrom in order to increase the amount of detectable signal.

In some embodiments, it is desirable to improve methods and systems for detecting nucleotide incorporation events as described herein by sustaining the signal to be detected. As discussed herein, in some embodiments the signal to be detected results from the incorporated nucleotide itself or a by-product therefrom. In addition to such signals being no more than stoichiometric as discussed above, the products directly produced by the nucleotide incorporation reaction may be transient in their existence. In some cases, this transience is due to the diffusion and/or neutralization of the reaction by-products. In some cases, the peak production of the signal is of a relatively short time frame, thereby requiring that the signal acquisition components of the systems or methods are configured to detect and/or capture this signal near or at its peak. In such embodiments, this desired detection window may require that a plurality of reaction sites acquire a corresponding plurality of signals in or near parallel. Thus, it is desirable in certain embodiments to convert the nucleotide incorporation event or by-products therefrom to a signal that is steady-state or sustained in time, thereby increasing the time window in which the sustained signal may be acquired.

In certain embodiments, the improved methods and systems for detecting nucleotide incorporation events involve the use of modified nucleotides. These modified nucleotides, examples of which are described herein (FIGS. 1-3), are suitable for modification covalently or non-covalently by a signal generating moiety. In some embodiments, the modification may occur after, during or before incorporation of the modified nucleotide into a nucleic acid strand. In some embodiments, the modified nucleotide includes a ligand moiety. In some embodiments, the ligand moiety is configured to bind specifically and/or with high affinity to a binding moiety. Examples of ligand moieties include, for example, biotin, cholesterol, digoxigenin, and other suitable antigens. Examples of binding moieties include, for example, avidin, streptavidin, cholesterol-binding antibody, digoxigenin binding antibody, and any suitable ligand-binding entity.

Figure 2:
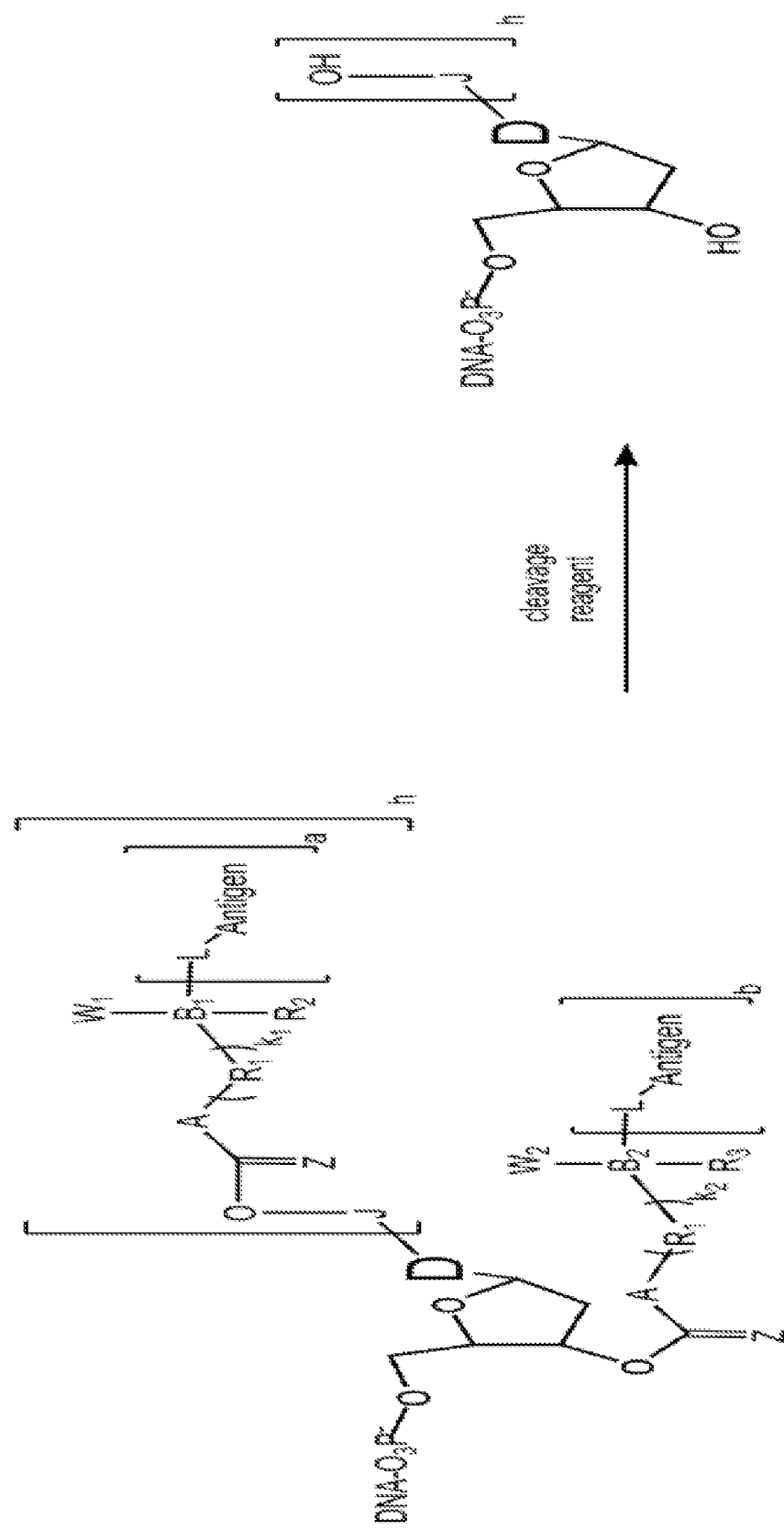
FIG. 2 shows several non-limiting examples of modified nucleotides.
Figure 3:
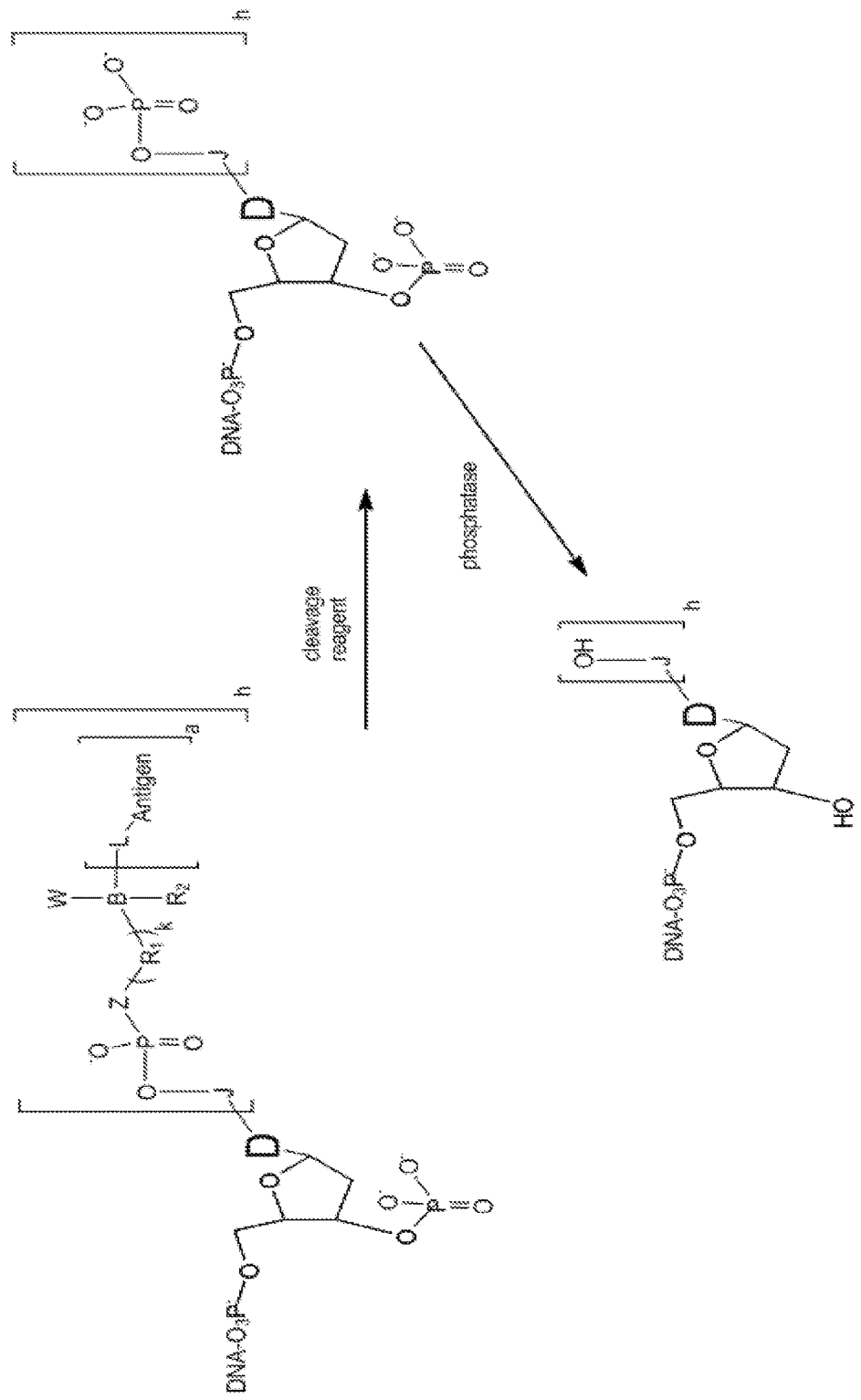
FIG. 3 shows several non-limiting examples of modified nucleotides.

In some embodiments, the binding moiety includes one or more signal generation moieties (FIGS. 1-3). In some embodiments, the signal generation entity is a catalytic enzyme that is capable of converting a substrate to a detectable signal (FIGS. 1-3). Examples of catalytic enzymes include, for example, alkaline phosphatases, peroxidases, luminases, and the like.

In some embodiments, the disclosure relates generally to methods, as well as related, systems, composition, kits and apparatuses, for incorporating a modified nucleotide and detecting an increased signal which is associated with generating a by-product of the nucleotide incorporation event. In some embodiments, exemplary embodiments of the modified nucleotides are shown in FIGS. 1-3.

In some embodiments, "D" is a base or analog thereof, including a purine or pyrimidine base or analog base thereof (FIGS. 1-3).

In some embodiments, "J", "L" and "B" represent linkers (FIGS. 1-3). Suitable linkers include, for example, substituted and unsubstituted alkyl linkers, substituted or unsubstituted polyether linkers, substituted or unsubstituted amide or ester linkers and the like.

In some embodiments, each occurrence of "h", "$m_1$", "$m_2$", "$n_1$", "$n_2$", "$k_1$", "$k_2$" can be independently a suitable integer, such as from 0 to 5 (FIGS. 1-3). In some embodiments, "$k_2$">2 and <13 (FIGS. 1-3). In some embodiments, when h=1, $n_2$=0, or when h=0, $n_2$=1. In some embodiments, each occurrence of "Z" and "A" can be independently $CH_2$, O, S, NH, or N-alkyl (FIGS. 1-3).

In some embodiments, "Affinity" includes any ligand moiety that can selectively bind a receptor (FIGS. 1-3). For example, "Affinity" includes one member of a binding partner that selectively binds the other member of the binding partner (e.g., receptor) (FIGS. 1-3). In a non-limiting example, the "Affinity" moiety includes biotin, digoxigenin, fluorescein, or cholesterol (FIGS. 1-3). In some embodiments, the "Affinity" moiety can bind a receptor moiety, including avidin, streptavidin, cholesterol-binding antibody, digoxigenin binding antibody, or any suitable ligand-binding entity (FIGS. 1-3). Many other examples of "Affinity" and receptor moieties are well known in the art (FIGS. 1-3). In some embodiments, the "Affinity" is linked to an enzyme (FIGS. 1-3). Optionally, the presence of the Affinity-enzyme complex is detected, and can also be quantified, by the presence of a product produced by the enzyme (FIGS. 1-3). Optionally, the enzyme comprises alkaline phosphatase (FIGS. 1-3).

In some embodiments, "J" is a linker connecting an oxygen atom to "D". In some embodiments, "J" comprises C1-C6 alkyl or alkyl amide, C3-C6 alkenyl or alkylenyl amide, C3-C6 alkynyl or alkynyl amide. In some embodiments, "J" is linked to the 7-position of a 7-deaza purine or analog thereof. In some embodiments, "J" is linked to the 5 position of pyrimidine or pyrimidine analog (FIGS. 1-3).

In some embodiments, the modified nucleotides can be cleaved by one or more hydrolytic agents or conditions (FIGS. 1-3). In some embodiments, the cleavage reagent can be a hydrolytic enzyme (e.g., a lipase, an esterase, a hydrolase, a phosphatase) (FIGS. 1-3). In some embodiments, the cleavage reagent can be a basic environment, such as changing the solution pH to 10 or greater (FIGS. 1-3). In some embodiments, the cleavage reagent can be a halogen anion, such as fluoride anion (FIGS. 1-3). In some embodiments, the cleavage reagent can be a metal cation, such as mercury (I or II) or silver anion (FIGS. 1-3).

In some embodiments, "Z" comprises O. In some embodiments, "$A_1$" comprises $CH_2$, O, S, NH or N-alkyl. In some embodiments, "$A_2$" comprises $CH_2$, O, S, NH or N-alkyl. In some embodiments, "$A_1$" and "$A_2$" are the same or different.

In some embodiments, "$R_1$" comprises methylene. In some embodiments, "$k_1$" can be >2 and <13. In some embodiments, "$k_2$" can be >2 and <13. In some embodiments, "B" is a linker. Optionally, "B" is between "L" and "$R_1$" (FIG. 1). Optionally, "B" comprises O, S, NH or substituted N. In some embodiments, "L" is a linker. Optionally, L is between the Affinity and B (FIG. 1).

In some embodiments, "$m_1$" can be zero or 1. In some embodiments, "$m_2$" can be zero or 1. In some embodiments, "$n_1$" can be zero or 1. In some embodiments, "$n_2$" can be zero or 1. In some embodiments, "h" can be zero or 1.

In some embodiments, when "h" is 1, the base "D" is operably linked to J, O, Z, $A_1$, $(R_1)k_1$, B, L, and Affinity (FIG. 1).

In some embodiments, when "$n_2$" is 1, the 3' position of the ribose or deoxyribose is linked to O, Z, $A_2$, $(R_1)k_2$, B, L and Affinity.

In some embodiments, "h" is 1 and "$n_2$" is zero. In some embodiments, "h" is 1 and "$n_2$" is 1. In some embodiments, "h" is zero and "$n_2$" is 1. In some embodiments, "h" is zero and "$n_2$" is zero.

In some embodiments, Z comprises O; A comprises $CH_2$, O, S, NH, or N-alkyl; $R_1$ comprises methylene; both $k_1$ and $k_2$>2 and <13; B comprises O, S, NH or substituted N; $m_1$ and $m_2$=1; and $n_1$ or $n_2$=1. Optionally, the cleaving agent comprises a lipase, esterase or pH>10.

In some embodiments, when h=1, the $A_1$ and $k_1$ do not have to equal $A_2$ and $k_2$.

In some embodiments, a cleaving agent removes a tag moiety linked to the base (e.g., when "h" is 1) and leaves a scar ("J-OH") (FIG. 1).

In some embodiments, a nucleotide incorporation reaction can be conducted with a mixture of modified nucleotides that include a first set of nucleotide molecules having "h" is 1 and "$n_2$" is zero, and a second set of nucleotide having "h" is zero and "$n_2$" is 1 (FIG. 1). Optionally, if the majority of the incorporated molecules are from "h"=0, "$n_2$"=0, then the majority of the DNA after signal detection and cleavage will have no scar. Optionally, detection of the incorporation event can be determined by the presence of the small % of base labeled molecules in the extended strand. Optionally, this nucleotide incorporation reaction can be used when the activity of molecules with "h"=0, "$n_2$"=1 is <<the activity of molecules with "h"=0, "$n_2$"=0, and the activity of molecules with "h"=1 and "$n_2$"=0 is similar to the molecules with "h"=0 and "$n_2$"=0 (FIG. 1).

In some embodiments, the disclosure relates generally to compositions, as well as related, systems, methods, kits and apparatuses, for a modified nucleoside comprising a nucleoside linked at the 3' position with a terminator group and/or linked at the base with a tag group. An exemplary embodiment is shown in FIG. 2.

In some embodiments, "D", "J", "L", and "Affinity" in FIG. 2 are the same as described for FIG. 1 above.

In some embodiments, "Z" comprises O. In some embodiments, "A" comprises S or O. In some embodiments, "$R_1$" comprises methylene or substituted methylene. In some embodiments, "$k_1$" and "$k_2$" are 1 or 2. In some embodiments, "$B_1$" and "$B_2$" comprise C or Si. In some embodiments, "$R_2$" and "$R_3$" comprise H, alkyl or trialkylsilyl. In some embodiments, "$W_1$" and "$W_2$" comprise H, alkyl or trialkylsilyl. In some embodiments, "b" is zero or 1 (FIG. 2).

In some embodiments, when "h" is 1, "b" is zero (FIG. 2). In some embodiments, when "h" is zero, "b" is 1 (FIG. 2).

In some embodiments, Z comprises O; A comprises S or O; $R_1$ comprises methylene or substituted methylene; $k_1$ and $k_2$=2; $B_1$ and $B_2$ comprise Si; $W_1$, $W_2$, $R_2$ and $R_3$ comprise alkyl. Optionally the cleaving agent comprises a fluoride anion (FIG. 2).

In some embodiments: Z comprises O; A comprises S or O; $R_1$ comprises methylene or substituted methylene; $k_1$ and $k_2$=1; $B_1$ and $B_2$ comprise C; $R_2$ and $R_3$ comprise H or alkyl; $W_1$ and $W_2$ comprise trialkylsilyl. Optionally, the cleaving agent comprises a fluoride anion (FIG. 2).

In some embodiments: Z comprises O; A comprises S or O; $R_1$ comprises methylene or substituted methylene; $k_1$=2 and $k_2$=1; $B_1$ comprises Si and $B_2$ comprises C; $W_1$ and $R_2$ comprise alkyl; $W_2$ comprises trialkylsilyl; and $R_3$ comprises H or alkyl. Optionally, the cleaving agent comprises a fluoride anion (FIG. 2).

In some embodiments: Z comprises O; A comprises S or O; $R_1$ comprises methylene or substituted methylene; $k_1$=1 and $k_2$=2; $B_1$ comprises C and $B_2$ comprises Si; $W_1$ comprises trialkylsilyl; $R_2$ comprises H or alkyl; $W_2$ and $R_3$ comprise alkyl. Optionally, the cleaving agent comprises a fluoride anion (FIG. 2).

In some embodiments, a nucleotide incorporation reaction can be conducted with a mixture of modified nucleotides that include a first set of nucleotide molecules having "h" is 1 and "b" is zero, and a second set of nucleotide having "h" is zero and "b" is 1 (FIG. 2).

In some embodiments, the disclosure relates generally to compositions, as well as related, systems, methods, kits and apparatuses, for a modified nucleoside comprising a nucleoside linked at the 3' position with a terminator group and/or linked at the base with a tag group. An exemplary embodiment is shown in FIG. 3.

In some embodiments, "D", "Affinity", "L" and "J" in FIG. 3 are the same as in FIG. 1 described above.

In some embodiments, "Z" comprises O or S (FIG. 3). In some embodiments, "A" comprises S or O (FIG. 3). In some embodiments, "$R_1$" comprises methylene or substituted methylene (FIG. 3). In some embodiments, "k" is 1-6 (FIG. 3). In some embodiments, "B" comprises O, N, S, C or Si (FIG. 3). In some embodiments, "$R_2$" comprises O, H, alkyl or trialkylsilyl (FIG. 3). In some embodiments, "W" comprises O, H, alkyl or trialkylsilyl. In some embodiments, "b" is zero or 1 (FIG. 3).

In some embodiments: Z comprises O; k=2; B comprises Si; W and $R_2$ comprise alkyl. Optionally, the first cleaving agent comprises a fluoride anion. Optionally, the second cleaving agent comprises a phosphatase (FIG. 3).

In some embodiments: Z comprises O, k=1; B comprises C; $R_2$ comprises H or alkyl; W comprises trialkylsilyl. Optionally, the first cleaving agent comprises a fluoride anion. Optionally, the second cleaving agent comprises a phosphatase (FIG. 3).

In some embodiments: Z comprises S; $R_1$ comprises methylene or substituted methylene; k=2-6; B comprises O, N, S or C; W comprises O, H, alkyl or nothing; $R_2$ comprises O, H, alkyl, or nothing. Optionally, the first cleaving agent comprises a silver cation or mercury cation. Optionally, the second cleaving agent comprises a phosphatase (FIG. 3).

Figure 4:
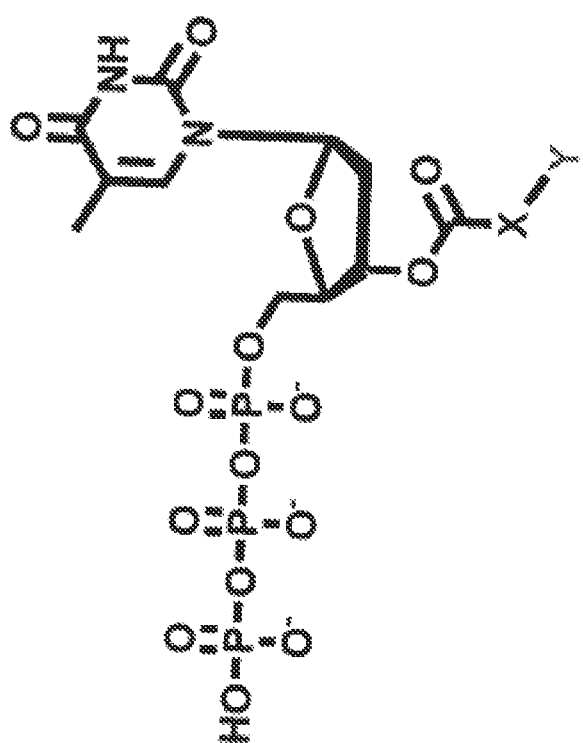
FIG. 4 shows a non-limiting example of a terminator nucleotide.

In some embodiments, the disclosure relates generally to compositions, as well as related, systems, methods, kits and apparatuses, for a modified nucleotide comprising any base (e.g., A, T, G, C, I or U), deoxyribose, and a triphosphate chain, where the 3' position of the deoxyribose is linked to a carbonyl group. For example, FIG. 4 shows a terminator nucleotide comprising a 3' carbonyl group, where X comprises NH, O or S. Optionally, Y is a detectable moiety "D" including one member of a binding partner (e.g., an affinity moiety such as biotin) or an optically detectable dye (e.g., a fluorphore). Optionally, the 3' terminator group is a carbonate, carbamate or thiocarbonate. Optionally, the 3' terminator group is cleavable with an enzyme, a chemical compound, acidic or basic conditions, heat, or light.

Figure 5:
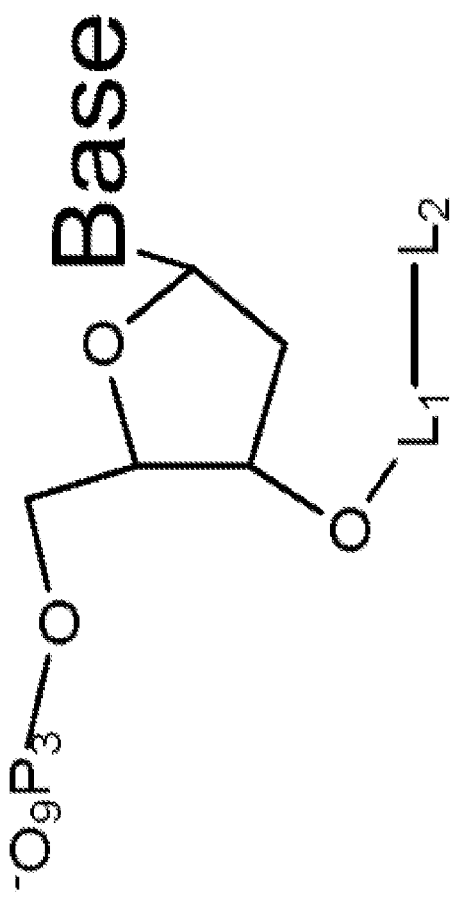
FIG. 5 shows a non-limiting example of a terminator nucleotide.

In some embodiments, the disclosure relates generally to compositions, as well as related, systems, methods, kits and apparatuses, for a modified nucleotide comprising, where the terminator group and/or the tag group comprises a neutral cleavable linkage group (e.g., lipophilic group) (FIG. 5). In some embodiments, the terminator group and/or the tag group comprises an anionic cleavable linker (e.g., hydrophilic) (FIG. 5). In some embodiments, the terminator group and/or the tag group comprises a neutral cleavable linker group and an anionic cleavable group (FIG. 5).

In some embodiments, the disclosure relates generally to compositions, as well as related, systems, methods, kits and apparatuses, for a terminator nucleoside comprising a purine or pyrimidine base and a ribose sugar, where the 2' OH or the 3' OH carbon position of the ribose is replaced with a terminator group. Optionally, the terminator group comprises a carbonyl moiety, including a carbonate or carbamate moiety. Optionally, the terminator group comprises an azide moiety. Optionally, the terminator group comprises a methyl or azido methyl moiety. Optionally, the terminator group comprises a carbonate moiety and an azido methyl moiety. Optionally, the terminator group comprises a carbamate moiety and an azido methyl moiety.

In some embodiments, the disclosure relates generally to compositions, as well as related, systems, methods, kits and apparatuses, for a terminator nucleoside comprising a purine or pyrimidine base and a deoxyribose sugar, where the 2' H or the 3' OH carbon position of the deoxyribose is replaced with a terminator group. Optionally, the terminator group comprises a carbonyl moiety, including a carbonate or carbamate moiety (FIG. 4). Optionally, the terminator group comprises an azide moiety. Optionally, the terminator group comprises a methyl or azido methyl moiety. Optionally, the terminator group comprises a carbonate moiety and an azido methyl moiety. Optionally, the terminator group comprises a carbamate moiety and an azido methyl moiety.

In some embodiments, the disclosure relates generally to methods, as well as related, systems, compositions, kits and apparatuses, for nucleic acid analysis. In some embodiments, nucleic acid analysis includes obtaining nucleic acid sequence information from a nucleic acid template molecule.

In some embodiments, the disclosure relates generally to methods, as well as related, systems, compositions, kits and apparatuses, for nucleic acid analysis that involve the use of modified nucleotides, including terminator nucleotides and/or tagged nucleotides, in a template-dependent nucleotide incorporation reaction (for example, a sequencing-by-synthesis reaction).

In some embodiments, the disclosure relates generally to methods, as well as related, systems, compositions, kits and apparatuses, for performing template-dependent nucleotide incorporation at a single reaction site, or at a plurality of reaction sites in an array of reaction sites. In some embodiments, at least one reaction site contains reagents for a conducting nucleotide incorporation reaction, including a nucleic acid template, an extendible end (e.g., provided by a primer or self-priming template or a nick), and a polymerase. In some embodiments, the nucleotide incorporation reaction is initiated at the reaction site by contacting the template, extendible end and polymerase with one or more nucleotides. In some embodiments, the one or more nucleotides are contained in a solution which is flowed into at least one reaction site that contains the template, extendible end and polymerase, thereby bringing the nucleotides into contact with the template, extendible end and polymerase. In some embodiments, the polymerase is a polymerase capable of incorporating a modified nucleotide into a nucleic acid strand. Optionally, the polymerase is a modified polymerase. Optionally, the reaction sites are in fluid communication with each other. Optionally, the nucleotides in the flow include at least one type of modified nucleotide, including terminator nucleotides and/or tagged nucleotides. Optionally, one type, or a mixture of different types of nucleotides may be flowed across the reaction site (each flow of nucleotide is termed a "nucleotide flow" herein), and incorporation will occur when an incoming nucleotide is complementary to the nucleotide in the template strand immediately adjacent to an extendible end of the primer (or the extendible end of a synthesized nucleic acid molecule). Optionally, the same type or different types of nucleotides are sequentially flowed across at least one reaction site. In some embodiments, one type or a mixture of different types of terminator nucleotides, tagged nucleotides and/or non-terminator nucleotides are flowed across at least one reaction site, and incorporation of a nucleotide (or lack thereof) is detected. Optionally, incorporation of the nucleotide is detected at the reaction site using a semiconductor sensor. Optionally, the semiconductor sensor detects a change in cleavage products from a nucleotide incorporation reaction.

In some embodiments, the disclosed nucleotide incorporation methods result in the formation and continued extension of a synthesized strand of nucleic acid, referred to herein as the "synthesized nucleic acid molecule" or the "synthesized strand" or "extended strand". The synthesized strand typically includes an extendible end (also referred to herein as a "polymerization initiation site"). The extendible end can serve as the site of nucleotide incorporation; incorporation of a nucleotide into the extendible end will result in the extension of the synthesized strand and increase in length of the synthesized strand by one nucleotide. Typically, the nucleotide incorporation is performed in a template-dependent manner where the identity of the incorporated nucleotide is determined based on the identity of an opposing nucleotide in the nucleic acid template, as dictated by a predetermined base pairing paradigm. The nucleotide incorporation can be performed using a polymerase (e.g., DNA or RNA polymerase) to polymerize one or more nucleotides. In some embodiments, the extendible end can include a terminal 3' OH group. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication. Thus, the extendible end may be at a terminal end or within a base-paired nucleic acid molecule. In other embodiments, the extendible end used by some polymerases (e.g., RNA polymerase) may not include a 3'OH group.

In some embodiments, the disclosure relates generally to methods, as well as related, systems, compositions, kits and apparatuses, for conducting a nucleotide incorporation reaction at one or more reaction sites. In some embodiments, at least one reaction site contains a complex having a polymerase bound to a nucleic acid template which has an extendible end, where the extendible end includes a terminal nucleotide having a 3'OH group. In some embodiments, the polymerase (as part of the complex) binds to an incoming terminator nucleotide (or tagged nucleotide), where the incoming terminator nucleotide (or tagged nucleotide) is complementary to a target nucleotide located on the nucleic acid template. In some embodiments, methods for conducting a nucleotide incorporation reaction comprises: (a) contacting (i) the polymerase which is part of a complex having a polymerase bound to a nucleic acid template having an extendible end and (ii) an incoming terminator nucleotide (or tagged nucleotide), wherein the complex is at a reaction site; and (b) catalyzing bond formation between the incoming terminator nucleotide (or tagged nucleotide) and a nucleotide at the extendible end, by polymerase-mediated phosphodiester bond formation between the incoming terminator nucleotide (or tagged nucleotide) and the nucleotide at the extendible end, with concomitant cleavage between the a and 3 phosphate groups of the incoming terminator nucleotide (or tagged nucleotide) to form a cleavage product. In some embodiments, the cleavage products include any one or a combination of heat, phosphate-based compounds, protons, and/or hydrogen ions. Optionally, the phosphate-based compounds include pyrophosphate. In some embodiments, the polymerase liberates the cleavage product. Optionally, the liberated cleavage product dissipates within the nucleotide incorporation reaction mixture and contacts at least one sensor located at a reaction site. In some embodiments, the sensor detects the presence of one or more cleavage products produced during incorporation of the terminator nucleotide (or tagged nucleotide). For example the sensor detects heat, phosphate-based compounds, protons, and/or hydrogen ions. In some embodiments, the cleavage products are non-optically detected by the sensors at the reaction sites. In some embodiments, the sensor detects the presence of one or more cleavage products which are produced by incorporation of the terminator nucleotide (or tagged nucleotide), and the sensor produces a signal. Thus, the signal produced by the sensor correlates with incorporation of the terminator nucleotide (or tagged nucleotide). Optionally, the method further comprises analyzing the signal produced by the sensor. Optionally, the method further comprises identifying the incorporated nucleotide. In some embodiments, the incoming terminator nucleotide (or tagged nucleotide) contacts the polymerase by performing a first nucleotide flow. In some embodiments, the terminator nucleotide that is incorporated contains a terminator group. In some embodiments, the terminator group is removable or can be transformed to become an extendible end (e.g., 3'OH end). In some embodiments, the terminator nucleotide that is incorporated includes adenosine, guanosine, cytosine, thymidine uridine, or inosine (hypoxanthine). In some embodiments, methods for conducting a nucleotide incorporation reaction further comprise incorporating a subsequent nucleotide, which optionally includes removing, cleaving or converting the terminator group on the incorporated terminator nucleotide to produce a 3'OH terminal end. In some embodiments, the terminator group (of the incorporated nucleotide) is removable by enzyme, chemical, light or heat, or can be transformed to become an extendible end (e.g., terminal 3'OH group). In some embodiments, the tagged group (of the incorporated nucleotide) is removable by enzyme, chemical, light or heat, or can be transformed to become an extendible end (e.g., terminal 3'OH group). In some embodiments, the polymerase-template complex at the reaction site can be contacted with a second nucleotide flow which contains terminator nucleotides and/or non-terminator nucleotides, and a second nucleotide is incorporated.

In some embodiments, the disclosure relates generally to methods, as well as related, systems, compositions, kits and apparatuses, for conducting a nucleotide incorporation reaction comprising: (a) providing a surface including one or more reaction sites containing (i) a polymerase and (ii) a nucleic acid template and (iii) an extendible end; (b) contacting one or more of the reaction sites with a first solution containing one or more types of terminator nucleotides having a terminator moiety; (c) incorporating at least one type of a terminator nucleotide at the extendible end within at least one of the reaction sites using the polymerase; and (d) detecting a product of the nucleotide incorporation within at least one of the reaction sites using a sensor that is attached or operatively linked to the at least one reaction site.

Optionally, the methods, as well as related, systems, compositions, kits and apparatuses further comprise: (e) removing, cleaving or converting the terminator moiety which is incorporated at the extendible end. Optionally, the methods, as well as related, systems, compositions, kits and apparatuses further comprise: (f) contacting one or more of the reaction sites with a second solution containing one or more types of terminator nucleotides having a terminator moiety; (g) incorporating at least one type of a terminator nucleotide at the extendible end within at least one of the reaction sites using the polymerase; and (h) detecting a product of the nucleotide incorporation within at least one of the reaction sites using a sensor that is attached or operatively linked to the at least one reaction site. Optionally, steps (a)-(h) can be repeated at least once.

Optionally, a different nucleic acid template is deposited at each of the one or more reaction sites.

Optionally, in steps (c) and (g), incorporating the terminator nucleotide at the extendible end generates a non-extendible end having a terminator moiety that inhibits incorporation of a subsequent non-terminator nucleotide or a terminator nucleotide.

Optionally, in step (e) the terminator moiety which is incorporated at the extendible end is contacted with a cleaving agent to remove or cleave the terminator moiety from the extendible end, or convert the terminator moiety to an extendible end. Optionally the cleaving agent includes an enzyme, a chemical compound, heat, or light.

Optionally, in steps (d) and (h), the sensor at the reactions sites detect a non-optical signal associated with incorporation of the terminator nucleotide.

Optionally, in steps (d) and (h), the sensor at the reactions sites detect a product of nucleotide incorporation, including heat, phosphate-based compounds, protons, and/or hydrogen ions.

Optionally, the one or more types of terminator nucleotides comprise a ribose or deoxyribose having a terminator moiety linked to the 2' or 3' or 4' position of the ribose or deoxyribose. Optionally, the one or more types of terminator nucleotides comprise a carbonyl terminator moiety. Optionally, the one or more types of terminator nucleotides comprise a carbonate or carbamate terminator moiety. Optionally, the one or more types of terminator nucleotides comprise an azide terminator moiety. Optionally, the one or more types of terminator nucleotides comprise an azido methyl moiety.

Optionally, the sensor comprises an ion-sensitive FET (isFET) or chemically-sensitive FET (chemFET).

Optionally, the surface contains a plurality of reaction sites, each site having one or more sensors. For example, the surface contains about 1-100 million, or about 100-250 million, or about 200-500 million, or about 500-900 million, or more reaction sites, where each reaction site is in contact with, operatively coupled, or capacitively coupled to one or more sensors that are ion-sensitive FETs (isFETs) or chemically-sensitive FETs (chemFETs) sensors. Optionally, the reaction sites are in fluid communication with each other.

Optionally, each reaction site, in the plurality of reaction sites, contains a nucleotide incorporation reaction that generates a nucleotide incorporation product, where the product is detected by the one or more isFET or chemFET sensors at each reaction site (e.g., in a massively parallel manner).

Optionally, about 100 million, or about 250 million, or about 500 million, or about 900 million reaction sites are separately detecting a nucleotide incorporation product generated in each of the these reaction site, where the product is detected by the one or more isFET or chemFET sensors at each reaction site.

In some embodiments, the disclosure relates generally to methods, as well as related, systems, compositions, kits and apparatuses, for detecting a plurality of nucleotide incorporations, comprising: (a) providing a surface having 100-700 million reaction sites (or more), wherein each reaction site is attached or operatively linked to at least one sensor, and each reaction site contains (i) a polymerase and (ii) a nucleic acid template and (iii) an extendible end, and wherein each reaction site includes nucleic acid templates that differ from other reaction sites; (b) contacting the reaction sites with a first solution containing one or more terminator nucleotides (e.g., having the same or different terminator moieties), wherein the reaction sites are in fluid communication with each other; (c) incorporating at least one type of a terminator nucleotide at the extendible end and generating a non-extendible end with a terminator moiety, and generating a nucleotide incorporation product within the reaction sites; and (d) detecting the product within the reaction sites using the sensor. Optionally, the individual reaction sites contain a plurality of nucleic acid templates having the same sequence. Optionally, the surface contains a plurality of reaction sites, and different reaction sites contain nucleic acid templates having different sequences. Optionally, the method further comprises the steps of: (e) removing, cleaving or converting the terminator moiety from the non-extendible end and generating an extendible end (e.g., 3'OH). Optionally, the methods further comprise: (f) contacting one or more of the reaction sites with a second solution containing one or more types of terminator nucleotides having a terminator moiety; (g) incorporating at least one type of a terminator nucleotide at the extendible end within at least one of the reaction sites using the polymerase; and (h) detecting a product of the nucleotide incorporation within at least one of the reaction sites using a sensor that is attached or operatively linked to the at least one reaction site. Optionally, steps (a)-(h) can be repeated at least once. Optionally, the 100-700 million reaction sites are attached or operatively linked to at least one isFET or chemFET. In some embodiments, the nucleotide incorporation produce includes heat, phosphate-based compounds (e.g., pyrophosphate), protons and/or hydrogen ions. In some embodiments, the first solution contains one type or a mixture of different types of terminator nucleotides. In some embodiments, the first solution contains a least one type of terminator nucleotides having a 3' carbonyl terminator moiety. Optionally, the 3' carbonyl terminator moiety comprises a carbonate or carbamate moiety. In some embodiments, a template polynucleotide having at least one homopolymeric region can be sequenced on an ion sensor using terminator nucleotides and/or tagged nucleotides (U.S. 2012/0052489, which are expressly incorporated herein by reference as if set forth in full).

In some embodiments, the disclosure relates generally to methods, as well as related, systems, compositions, kits and apparatuses, for sequence-by-synthesis reactions conducted with terminator nucleotides in conjunction with non-optical detection of nucleotide incorporation.

In some embodiments, the disclosure relates generally to methods, as well as related, systems, compositions, kits and apparatuses, involve a reaction site or array of reaction sites, where independent nucleotide incorporation reactions occur at or near the reaction sites in the array. Optionally, the reaction site (or one or more reaction sites within an array of reaction sites) is attached or operatively linked to a non-optical sensor. In some embodiments, different reaction sites in the array are attached or operatively linked to different sensors. In some embodiments, at least two of the reaction sites are attached or operatively linked to the same sensor. The sensor can be configured to detect a non-optical signal that indicates a template-dependent nucleotide incorporation occurring at the reaction site or sites to which it is attached or operatively linked. In some embodiments, the non-optical signal does not include photon emissions. In some embodiments, the nucleotide incorporation can include incorporation of a terminator nucleotide. In some embodiments, the nucleotide incorporation can include incorporation of a non-terminator nucleotide. The terminator nucleotide may include a reversible or a non-reversible terminator moiety. The reversible terminator moiety may be removable. For example, the reversible terminator moiety may be removed through physical or chemical treatments.

Optionally, the terminator nucleotide does not include an optically detectable label. In some embodiments, the terminator nucleotide does not include a fluorescent or luminescent label. In some embodiments, the terminator nucleotide does not include a label that can be detected spectrally.

In some embodiments, the disclosure relates generally to methods, as well as related, systems, compositions, kits and apparatuses, can involve detection of the non-optical signal using a sensor attached to, or operatively linked to, the reaction site or sites. In some embodiments, the non-optical signal is a chemical signal indicating the release of nucleotide incorporation byproducts or generation of other chemical moieties. In some embodiments, the non-optical signal quantitatively indicates nucleotide incorporation. Optionally, the non-optical signal is a pH based signal. The pH based signal can be generated via the release of hydrogen ion byproducts during nucleotide incorporation. In some embodiments, the non-optical signal includes generation of phosphate or other ions at the reaction site or sites. In some embodiments, the non-optical signal includes generation of heat at the reaction site or sites.

In some embodiments, a series of nucleotide flows across the reaction site are performed. Optionally, some or all of the nucleotide flows include terminator nucleotides, non-terminator nucleotides, or a mixture of terminator and non-terminator nucleotides.

One skilled in the art will appreciate that a series of nucleotide flows can contain, in any given flow, a single type of terminator or non-terminator nucleotides, a mixture of different terminator nucleotides, a mixture of different non-terminator nucleotides, or a mixture of terminator and non-terminator nucleotides. A first flow can contain the same terminator or non-terminator nucleotides (single type or a mixture) as a subsequent flow.

For example, a first flow containing a first single type of terminator nucleotide is succeeded by a second flow containing a second single type of terminator nucleotide, where the first and the second flows contain the same type or a different type of terminator nucleotide.

In another example, a first flow containing a first single type of terminator nucleotide is succeeded by a second flow containing a second single type of non-terminator nucleotide.

In another embodiment, a first flow containing a mixture of two or more different types terminator nucleotides is succeeded by a second flow containing a single type of terminator nucleotides.

In yet another example, a first flow containing a mixture of two or more different types terminator nucleotides is succeeded by a second flow containing a mixture of two or more different types terminator nucleotides, where the first and the second flows contain the same mixture terminator nucleotides or contain a different mixture of terminator nucleotides.

In some embodiments, a first series of nucleotide flows is succeeded by a denaturing step. For example, the denaturing step can involve application of heat and/or chemicals that denature the synthesized strand from the template strand. In some embodiments, the denaturing step includes performing a denaturing flow. The denaturing flow can include flow of a denaturing agent (e.g. urea, formamide, alkali, NaOH and the like) across one or more reaction sites. The reaction sites can each act as a site for sequencing by synthesis. The denaturing agent can denature the synthesized strand from the template strand. Optionally, a first series of nucleotide flows is succeeded by a denaturing flow, following by a second series of nucleotide flow.

In some embodiments, the disclosure relates generally to methods, as well as related, systems, compositions, kits and apparatuses, for generating a nucleic acid having a non-extendible end, comprising: (a) contacting a nucleic acid template with an oligonucleotide primer having a 3' terminal extendible end, a polymerase and a terminator nucleotide; and (b) incorporating the terminator nucleotide into the 3' terminal extendible end to generate an oligonucleotide primer having a 3' non-extendible end. In some embodiments, the terminator nucleotide comprises a ribose or deoxyribose having a terminator moiety linked to the 2' or 3' or 4' position of the ribose or deoxyribose. Optionally, the terminator nucleotide comprises a carbonyl terminator moiety. Optionally, the terminator nucleotide comprises a carbonate or carbamate terminator moiety. Optionally, the terminator nucleotide comprises an azide terminator moiety. Optionally, the terminator nucleotide comprises an azido methyl moiety. Optionally, the 3' non-extendible end of the oligonucleotide primer contains a terminator moiety which is an azide or an azido methyl moiety. Optionally, the method further comprises: (c) contacting the 3' non-extendible end (of the oligonucleotide primer) with a cleaving agent to remove the terminator moiety to generate an oligonucleotide primer having an extendible 3' terminal end. Optionally, the cleaving agent comprises a phosphine compound, including Tris(2-carboxyethyl)phosphine (TCEP). Optionally steps (a), (b) and (c) can be repeated at least once.

The ability of enzymes to catalyze biological reactions is fundamental to life. A range of biological applications use enzymes to synthesize various biomolecules in vitro. One particularly useful class of enzymes is the polymerases, which can catalyze the polymerization of biomolecules (e.g., nucleotides or amino acids) into biopolymers (e.g., nucleic acids or peptides). For example, polymerases that can polymerize nucleotides into nucleic acids, particularly in a template-dependent fashion, are useful in recombinant DNA technology and nucleic acid sequencing applications. Several nucleic acid sequencing methods (including some of the methods discussed herein) monitor nucleotide incorporations during in vitro template-dependent nucleic acid synthesis catalyzed by a polymerase.

Polymerases are also useful for the generation of nucleic acid libraries, such as libraries created during PCR, such as ligation mediated PCR, emulsion PCR and bridge PCR. Nucleic acid libraries created using such polymerases can be used in a variety of downstream processes, such as genotyping, nucleotide polymorphism (SNP) analysis, copy number variation analysis, epigenetic analysis, gene expression analysis, hybridization arrays, analysis of gene mutations including but not limited to detection, prognosis and/or diagnosis of disease states, detection and analysis of rare or low frequency allele mutations, forensic analyses, detection of genomic sites or regions susceptible to pharmacological treatment, and nucleic acid sequencing including but not limited to de novo sequencing, whole genome amplification, pre-implantation genetic sequencing or targeted resequencing.

In some embodiments, the disclosure relates generally to methods, as well as related, systems, compositions, kits and apparatuses, for incorporating modified nucleotides (e.g., terminator nucleotides and/or tagged nucleotides) into a nucleic acid strand with a polymerase. In some embodiments, the methods, as well as related, systems, compositions, kits and apparatuses include using one or more polymerases for incorporating modified nucleotides, extending an initiation site (e.g., extending a primer), or amplifying nucleic acids. When performing polymerase-dependent nucleic acid synthesis or amplification, it can be useful to modify the polymerase (for example via mutation or chemical modification) so as to alter its catalytic properties. In some instances, it can be useful to modify the polymerase by way of amino acid substitution to enhance its catalytic or DNA binding properties. Polymerase performance in various biological assays involving nucleic acid synthesis or amplification can be limited by the kinetic behavior of the polymerase towards individual nucleotide substrates. For example, analysis of polymerase activity can be complicated by undesirable behaviors such as the tendency of a given polymerase to dissociate from a template; to bind and/or incorporate the incorrect (e.g., non Watson-Crick base-paired) nucleotide; or to release the correct (e.g., Watson-Crick based paired) nucleotide without incorporation. Other complications can arise when using modified nucleotides as substrates for incorporation during polymerization, such as the use of blocked (e.g., terminated) or reversibly blocked (e.g., unblocked) nucleotides. Many different forms of blocked and reversibly blocked nucleotides are known in the art. Of particular interest, are 2' or 3' or 4' reversibly blocked nucleotides, which often include one or more linkers that can hinder or inhibit the performance of a polymerase during nucleic acid synthesis. Thus, it is desirable when using 2' or 3' or 4' reversibly blocked nucleotides to develop a modified polymerase capable of incorporating such reversibly blocked substrates during polymerization. These polymerase properties can be enhanced via suitable selection, engineering and/or modification of a polymerase of choice. For example, such modification can be performed to favorably alter the polymerase's rate of nucleotide incorporation, affinity of binding to template, processivity or average read length; such alterations can increase the amount of sequence information obtained from a single sequencing reaction.

There remains a need in the art for improved polymerase compositions exhibiting altered, e.g., increased processivity, read length (including error-free read length) and/or affinity for DNA templates and in particular for modified polymerase compositions capable of incorporating 2' or 3' or 4' reversibly blocked nucleotides during amplification, polymerization or nucleic acid synthesis. Such polymerase compositions can be useful in a wide variety of assays involving polymerase-dependent nucleic acid synthesis, including nucleic acid sequencing and production of nucleic acid libraries.

In some embodiments, the disclosure relates generally to polymerase compositions, methods of making and using the same. In some embodiments, the disclosure relates generally to one or more modified polymerases, wherein the one or more modified polymerases contain at least one amino acid substitution as compared to a reference polymerase (e.g., a corresponding polymerase lacking the at least one amino acid substitution). In some embodiments, the disclosure relates generally to a composition (and methods of use thereof) comprising a modified DNA or RNA polymerase. In some embodiments, the composition includes a modified polymerase from an A family DNA polymerase or a B family DNA polymerase. In some embodiments, the disclosure relates generally to a modified polymerase having at least one amino acid substitution, where the amino acid substitution enhances or improves processivity of the at least one modified polymerase as compared to the processivity of a reference (e.g., unmodified) polymerase. In some embodiments, processivity can include a comparison of mean read lengths (MRL) obtained using the modified polymerase and the unmodified (or reference) polymerase in a nucleic acid polymerization or sequencing reaction. In some embodiments, processivity can include a comparison of MRL, total number of sequencing reads, percentage of end-to end reads, among other metrics, obtained from a nucleic acid sequencing reaction. In some embodiments, the disclosure relates generally to a polymerase (and methods of use thereof) for nucleic acid sequencing, including but not limited to next-generation sequencing and/or sequencing by synthesis.

In some embodiments, the disclosure relates generally to a modified polymerase composition (and methods of use thereof) for the generation of nucleic acid libraries or nucleic acid templates.

In some embodiments, the disclosure relates generally to a modified polymerase composition (and methods of use thereof) for polymerization of nucleic acids. In some embodiments, the method includes polymerizing at least one modified nucleotide or modified nucleotide analog, including but not limited to 2' or 3' or 4' blocked (terminated) nucleotides to a template, nucleic acid, primer or probe. In some embodiments, the method includes polymerizing at least one modified nucleotide or modified nucleotide analog, including but not limited to 2' or 3' or 4' reversibly blocked (non-terminated) nucleotides to a template, primer, probe or nucleic acid.

In some embodiments, the modified polymerase includes a polymerase capable of performing nucleic acid sequencing on an ISFET. In some embodiments, the disclosure generally relates to a method of nucleic acid polymerization on an ISFET or ChemFET, where the method includes contacting a template, primer, and substrate suitable for polymerization with a modified polymerase; and incorporating onto the primer or substrate suitable for polymerization an additional nucleotide or nucleotide analog, including but not limited to a 2' or 3' or 4' reversibly blocked nucleotide. In some embodiments, the method includes a modified polymerase having at least one amino acid substitution relative to a reference or unmodified polymerase, and where the modified polymerase includes increased processivity as compared to the reference or unmodified polymerase. In another embodiment, the modified polymerase comprises a polymerase capable of performing nucleic acid polymerization and/or nucleic acid sequencing on a flow cell.

In some embodiments, the disclosure relates to compositions, methods, systems, apparatuses and kits that contain one or more of the modified polymerases, where the modified polymerase is capable of incorporating at least one 2' or 3' or 4' reversibly blocked nucleotide. In some embodiments, the modified polymerase capable of incorporating a 2' or 3' or 4' reversibly blocked nucleotide can include incorporation in a template-dependent manner. In some embodiments, the compositions, methods, systems, apparatuses and kits can be used for synthesizing a DNA or RNA strand. In some embodiments, the 2' or 3' or 4' reversibly blocked nucleotide may optionally include an additional modification to base of the 2' or 3' or 4' reversibly blocked nucleotide.

In some embodiments, the compositions, methods, systems, apparatuses and kits containing one or more modified polymerases capable of incorporating a 2' or 3' or 4' reversibly blocked nucleotide can amplify at least 10, 50, 100, 500, 1000, 2500, 5000, 7500, 10000, 25000, 50000, 100000, 500000, or more nucleic acid templates in a single reaction.

In some embodiments, the disclosure relates generally to a method for performing a nucleotide polymerization reaction comprising or consisting of contacting a modified polymerase or a biologically active fragment thereof with a nucleic acid template in the presence of a 2' or 3' or 4' reversibly blocked nucleotide, where the modified polymerase or the biologically active fragment thereof includes at least one amino acid modification relative to a reference polymerase (e.g., an unmodified polymerase), and polymerizing the 2' or 3' or 4' reversibly blocked nucleotide using the modified polymerase or the biologically active fragment thereof. In some embodiments, the method includes a modified polymerase or biologically active fragment thereof having increased processivity relative to the reference polymerase (e.g., unmodified polymerase).

In some embodiments, the at least one amino acid modification relative to a reference polymerase can include one or more amino acid substitutions relative to the reference polymerase. In another embodiment, the at least one amino acid modification can include a substitution of a first domain or motif from a first polymerase species or family with a homologous or corresponding domain or motif from a second polymerase species or family. In one embodiment, the modified polymerase can include a chimeric polymerase. In some embodiments, a chimeric polymerase can comprise a first domain or motif from a first polymerase operably linked to a second domain or motif from a second polymerase, wherein each domain or motif retains its functionality in the chimeric polymerase. In some embodiments, a chimeric polymerase can include a first domain or motif from a first polymerase, a second domain or motif from a second polymerase, and a third domain or motif from a third polymerase, wherein each domain or motif retains its functionality in the chimeric polymerase.

In some embodiments, the modified polymerase can include a first domain or motif from a first polymerase (e.g., a KOD polymerase), wherein the first domain or motif enhances or improves processivity as compared to the unmodified polymerase, and a second domain or motif from a second polymerase (e.g., Bst DNA polymerase), wherein the second domain or motif enhances or improves association of the polymerase with a nucleic acid template as compared to the unmodified polymerase. In some embodiments, the modified polymerase includes one or more domains (e.g., a DNA binding domain or a catalytic domain) that enhance or improve incorporation of a 2' or 3' or 4' reversibly blocked nucleotide. In another embodiment, the modified polymerase can include a first domain and a second domain from two distinct family B polymerases. In one embodiment, the modified polymerase can include a first domain and second domain from two distinct family A polymerases.

In some embodiments, the method includes polymerizing at least one 2' or 3' or 4' reversibly blocked nucleotide using the modified polymerase or the biologically active fragment thereof in the presence of a high ionic strength solution. In some embodiments, the high ionic strength solution can be about 100 mM to about 500 mM salt. In some embodiments, the high ionic strength solution can be about 115 mM to about 400 mM salt. In some embodiments, the high ionic strength solution can be about 125 mM to about 300 mM salt. In some embodiments, the high ionic strength solution can be about 150 mM to about 250 mM salt. In some embodiments, the salt can include a potassium and/or sodium salt, such as KCl and/or NaCl. It will be apparent to the skilled artisan that various other suitable salts can be used in place, or in combination with KCl and/or NaCl. In some embodiments, the ionic strength solution can further include a sulfate.

In some embodiments, the method can further include polymerizing the at least one 2' or 3' or 4' reversibly blocked nucleotide in a template-dependent fashion. In some embodiments, the method can further including hybridizing a primer to the template prior to, during or after the contacting, and where the polymerizing includes polymerizing at least one 2' or 3' or 4' reversibly blocked nucleotide onto an end of the primer using the modified polymerase or the biologically active fragment thereof.

In some embodiments, the polymerizing is performed in the proximity of a sensor that is capable of detecting the polymerization of the 2' or 3' or 4' reversibly blocked nucleotide by the modified polymerase or the biologically active fragment thereof. In another embodiment, the sensor is capable of detecting cleavage of the one or more linkers present on the 2' or 3' or 4' reversibly blocked nucleotide after polymerization. In some embodiments, the method can further include detecting a signal indicating polymerization of the 2' or 3' or 4' reversibly blocked nucleotide by the modified polymerase or the biologically active fragment thereof using a sensor. In some embodiments, the sensor is an ISFET.

In some embodiments, the disclosure generally relates to a method for performing nucleic acid amplification comprising or consisting of generating an amplification reaction mixture having a modified polymerase or a biologically active fragment thereof, a primer, a nucleic acid template, and one or more 2' or 3' or 4' reversibly blocked nucleotides, where the modified polymerase or the biologically active fragment thereof includes one or more amino acid modifications relative to a reference polymerase; and subjecting the amplification reaction mixture to amplifying conditions, where at least one of the one or more 2' or 3' or 4' reversibly blocked nucleotides is polymerized onto the end of the primer using the modified polymerase or the biologically active fragment thereof. In some embodiments, the modified polymerase includes a modified polymerase capable of incorporating at least one 2' or 3' or 4' reversibly blocked nucleotide and has increased processivity relative to the reference polymerase. In some embodiments, the one or more amino acid modifications relative to a reference polymerase can include one or more amino acid substitutions relative to the reference polymerase that improves or enhances incorporation of a 2' or 3' or 4' reversibly blocked nucleotide as compared to the reference polymerase (e.g., a polymerase lacking the corresponding amino acid substitutions).

In some embodiments, the method comprises or consists of determining the identity of the 2' or 3' or 4' reversibly blocked nucleotide. In some embodiments, the method can further include cleaving one or more linkers from the incorporated 2' or 3' or 4' reversibly blocked nucleotide, wherein the cleaving produces a free 2' or 3' or 4' group capable of undergoing a subsequent nucleotide incorporation reaction (e.g., incorporation of a natural nucleotide, modified nucleotide, or 2' or 3' or 4' reversibly blocked nucleotide). In one embodiment, the method can further include detecting a byproduct released during polymerization of the 2' or 3' or 4' reversibly blocked nucleotide. In some embodiments, the byproduct is an ion. In one embodiment, the byproduct is a hydrogen ion. In another embodiment, the byproduct is a pyrophosphate ion.

In some embodiments, the disclosure generally relates to a method of detecting a change in ion concentration after a nucleotide polymerization reaction comprising or consisting of performing a nucleotide polymerization reaction using a modified polymerase or a biologically active fragment in the presence of at least one 2' or 3' or 4' reversibly blocked nucleotide, incorporating a 2' or 3' or 4' reversibly blocked nucleotide thereby forming a ion byproduct, and detecting a change in ion concentration. In one embodiment the ion byproduct is a hydrogen ion or a pyrophosphate ion. In some embodiments, the method further includes detecting a signal indicating the change in ion concentration during or after incorporation of a 2' or 3' or 4' reversibly blocked nucleotide.

As used herein, the term "polymerase" and its variants comprise any enzyme that can catalyze the polymerization of nucleotides (including blocked or reversibly blocked nucleotides including but not limited to 2' or 3' or 4' reversibly blocked nucleotides) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion, chimeric or otherwise engineered polymerases, chemically modified polymerases, synthetic molecules or assemblies, and any analogs, homologs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts, domains, or motifs of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and E. coli DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a processivity-enhancing domain.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; between a nucleotide and a label; and the like. Some examples of linkages can be found, for example, in Hermanson, G., *Bioconjugate Techniques*, Second Edition (2008); Aslam, M., Dent, A., *Bioconjugation: Protein Coupling Techniques for the Biomedical Sciences*, London: Macmillan (1998); Aslam, M., Dent, A., *Bioconjugation: Protein Coupling Techniques for the Biomedical Sciences*, London: Macmillan (1998).

The terms "modification" or "modified" and their variants, as used herein with reference to polypeptide or protein, for example a polymerase, comprise any change in the structural, biological and/or chemical properties of the protein. In some embodiments, the modification can include a change in the amino acid sequence of the protein. For example, the modification can optionally include one or more amino acid mutations, including without limitation amino acid additions, deletions and substitutions (including both conservative and non-conservative substitutions). In some embodiments, the modification can include an amino acid substitution that improves or enhances processivity as compared to a reference polymerase lacking the one or more processivity based amino acid substitutions. In some embodiments, the modification can optionally include one or more amino acid mutations, including insertions or deletions that change the surface structure of the protein.

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, or isoleucine) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

Proteins and/or protein subsequences (such as biologically active fragments) are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or biologically active fragments or sequences thereof). The precise percentage of similarity between sequences that is useful in establishing homology varies with the nucleic acid and protein at issue, but as little as 50% sequence similarity over 25, 50, 100, 150, or more nucleic acids or amino acid residues, is routinely used to establish homology. Higher levels of sequence similarity, e.g., 50%, 60%, 70%, 80%, 85%, 90%, 95%, 98% or 99%, can also be used to establish homology.

Methods for determining sequence similarity percentages (e.g., BLASTP and BLASTN using default parameters) are described herein and are generally available. For sequence comparison and homology determination, typically one sequence acts as a reference sequence to which test sequences are compared. Generally, when using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004). One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length "W" in the query sequence, which either match or satisfy some positive-valued threshold score 'T' when aligned with a word of the same length in a database sequence. 'T' is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using for nucleotide sequences the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters "W", 'T', and "X" determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

The term "primer extension activity" and its variants, as used herein, when used in reference to a given polymerase, comprise any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. In some embodiments, the primer extension activity of a given polymerase can be quantified as the total number of nucleotides incorporated (as measured by, e.g., radiometric or other suitable assay) by a unit amount of polymerase (in moles) per unit time (seconds) under a particular set of reaction conditions.

The term "DNA binding activity" and its variants, as used herein, when used in reference to a given polymerase, comprise any in vivo or in vitro enzymatic activity characteristic of a given polymerase that relates to interaction of the polymerase with a DNA sequence in a recognition-based manner. Typically but not necessarily such interaction includes binding of the polymerase, and more specifically binding of the DNA-binding domain of the polymerase, to the recognized DNA sequence. In some embodiments, recognition includes binding of the polymerase to a sequence-specific or non-sequence specific DNA sequence. In some embodiments, the DNA binding activity of a given polymerase can be quantified as the affinity of the polymerase to recognize and bind to the recognized DNA sequence. For example, DNA binding activity can be monitored and determined using an anistrophy signal change (or other suitable assay) as a protein-DNA complex is formed under a particular set of reaction conditions.

As used herein, the term "biologically active fragment" and its variants, when used in reference to a given biomolecule, refers to any fragment, derivative, homolog or analog of the biomolecule that possesses an in vivo or in vitro activity that is characteristic of the biomolecule itself. For example, a polymerase can be characterized by various biological activities, for example DNA binding activity, nucleotide polymerization activity, primer extension activity, strand displacement activity, reverse transcriptase activity, nick-initiated polymerase activity, 3'-5' exonuclease (proofreading) activity, and the like. In some embodiments, a "biologically active fragment" of a polymerase is any fragment, derivative, homolog or analog of the polymerase that can catalyze the polymerization of nucleotides (including but not limited to 2' or 3' or 4' reversibly blocked nucleotides) into a nucleic acid strand. In some embodiments, the biologically active fragment, derivative, homolog or analog of the polymerase possesses 10%, 20%, 30%, 40%, 50%, 60%, 70%, 75%, 80%, 85%, or 90% or greater, of the biological activity of the polymerase in any in vivo or in vitro assay of interest such as, for example: DNA binding assays, nucleotide polymerization assays (which may be template-dependent or template-independent), primer extension assays, strand displacement assays, reverse transcriptase assays, proofreading assays, and the like. In some embodiments, the biological activity of a polymerase biologically active fragment can be assayed by measuring the in vitro processivity of the polymerase biologically active fragment under defined reaction conditions (for example, measuring mean read length). In some embodiments, the biological activity of a polymerase biologically active fragment can be assayed by measuring the primer extension activity in vitro of the polymerase biologically active fragment under defined reaction conditions. In some embodiments, the biological activity of a polymerase biologically active fragment can be assayed by measuring the polymerization activity in vitro of the polymerase biologically active fragment under defined reaction conditions. In some embodiments, the biological activity of a polymerase fragment can be assayed by measuring the DNA binding activity in vitro of the fragment under defined reaction conditions. In some embodiments, the biological activity of a polymerase fragment can be assayed by measuring the strand displacement activity in vitro of the fragment under defined reaction conditions. In some embodiments, the biological activity of a polymerase fragment can be assayed by measuring the reverse transcriptase activity in vitro of the fragment under defined reaction conditions. In some embodiments, the biological activity of a polymerase fragment can be assayed by measuring the proofreading activity in vitro of the fragment under defined reaction conditions. In some embodiments, the biologically active fragment of a polymerase can include measuring the biological activity of any one or more of the polymerase biological activities outlined herein.

In some embodiments, a biologically active fragment can include any part of the DNA binding domain or any part of the catalytic domain of the modified polymerase. It will be readily apparent to the skilled artisan that the DNA binding and catalytic domains even among closely related polymerases can differ with respect to the absolute number or sequence of amino acid residues. Members of a polymerase family that are evolutionary related will likely share a high degree of sequence homology. It will also be apparent to the skilled artisan that the binding domain or the catalytic domain of a polymerase of interest can be determined using standard methods known to one of skill in the art. For example, crystallography, atomic force microscopy and various biochemical assays can be used to determine the amino acid motif of each domain. In some embodiments, the biologically active fragment of a modified polymerase can optionally include any 25, 50, 75, 100, 150 or more contiguous amino acid residues of the DNA binding or catalytic domain. In some embodiments, a biologically active fragment of the modified polymerase can include at least 25 contiguous amino acid residues of the catalytic domain or the DNA binding domain having at least 80%, 85%, 90%, 95%, 98%, or 99% identity to any one or more of the polymerases encompassed by the disclosure.

Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells.

In some embodiments, the disclosure relates generally to not only the specific polymerases disclosed herein, but also to any biologically active fragment of such polymerases, which are encompassed within the scope of the present disclosure. In some embodiments, a biologically active fragment of any polymerase of the disclosure includes any fragment that exhibits primer extension activity in vitro. In some embodiments, a biologically active fragment of any polymerase of the disclosure includes any fragment that exhibits DNA binding activity in vitro. In some embodiments, a biologically active fragment of any polymerase of the disclosure includes any fragment that retains polymerase activity in vitro. In some embodiments, a biologically active fragment of any polymerase of the disclosure includes any fragment capable of polymerizing incorporation of at least one 2' or 3' or 4' reversibly blocked nucleotide. Polymerase activity can be determined by any method known in art. For example, determination of polymerase activity can be based on the activity of extending a primer on a template.

In some embodiments, the disclosure generally relates to a modified polymerase having one or more amino acid mutations (such as a deletion, substitution or addition) relative to a reference polymerase lacking the one or more amino acid mutations, and wherein the modified polymerase retains polymerase activity in vitro, exhibits primer extension activity in vitro, or incorporates at least one 2' or 3' or 4' reversibly blocked nucleotide to one end of a primer under suitable polymerization conditions. In some embodiments, the modified polymerase includes any biologically active fragment of such polymerase that retains polymerase activity in vitro, exhibits primer extension activity in vitro, or incorporates at least one 2' or 3' or 4' reversibly blocked nucleotide to one end of a primer under suitable polymerization conditions. In some embodiments, the compositions, methods, kits, apparatuses and systems of the instant disclosure include modified polymerases having the in vitro ability to exhibit primer extension activity, wherein the primer extension includes incorporation of at least one reversibly blocked nucleotide. In some embodiments, the reversibly blocked nucleotide includes a 2' or 3' or 4' reversibly blocked nucleotide.

As used herein, the term "nucleotide" and its variants comprise any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. In some embodiments, the nucleotide can comprise a blocked nucleotide (e.g., a modified nucleotide that once incorporated into a nucleic acid strand cannot be readily cleaved from the nucleic acid strand to generate a free 3'OH group for further nucleotide extension) or reversibly blocked nucleotide. In some embodiments, the nucleotide can include a 2' or 3' or 4' reversibly blocked nucleotide. Optionally, the 2' or 3' or 4' reversibly blocked nucleotide can further include at least one modification to the base. In some embodiments, the at least one modification is attached to the base via a linker.

As used herein, the term "nucleotide incorporation" and its variants comprise polymerization of one or more nucleotides to form a nucleic acid strand including at least two nucleotides linked to each other, typically but not necessarily via phosphodiester bonds, although alternative linkages may be possible in the context of particular nucleotide analogs. In some embodiments, polymerization of the one or more nucleotides can include polymerization of a blocked or reversibly blocked nucleotide, including but not limited to, a 2' or 3' or 4' reversibly blocked nucleotide to a second nucleotide. Optionally, the second nucleotide is a blocked or reversibly blocked nucleotide.

As used herein, the term "processivity" and its variants comprise the ability of a polymerase to remain bound to a single primer/template hybrid. In some embodiments, processivity can be measured by the number of nucleotides that a polymerase incorporates into a nucleic acid (such as a sequencing primer) prior to dissociation of the polymerase from the primer/template hybrid. In some embodiments, the polymerase has a processivity of at least 100 nucleotides, although in other embodiments it has a processivity of at least 200 nucleotides, at least 300 nucleotides, at least 400 nucleotides, at least 500 nucleotides or greater. It will be understood by those of ordinary skill in the art that the higher the processivity of the polymerase, the more nucleotides that can be incorporated prior to dissociation and therefore the longer the sequence (read-length) that can be obtained. In other words, polymerases having low processivity will typically provide shorter average read-lengths than polymerases having higher processivity. In one embodiment, polymerases of the instant disclosure containing one or more amino acid mutations can possess enhanced processivity as compared to a reference polymerase lacking the one or more amino acid mutations.

In one exemplary assay, the processivity of a given polymerase can be measured by incubating the polymerase with a primer:template duplex under nucleotide incorporation conditions, and resolving the resulting primer extension products using any suitable method, for example via gel electrophoresis. The primer can optionally include a label to enhance detectability of the primer extension products. The nucleotide incorporation reaction mixture typically includes a vast excess of unlabeled competitor template, thereby ensuring that virtually all of the extension products are produced through a single template binding event. Following such resolution, the average amount of full-length extension product can be quantified using any suitable means, including fluorimetric or radiometric detection of full-length extension products. To compare the processivity of two or more different polymerases (e.g., a reference and modified polymerase), each polymerase can be employed in a parallel and separate reaction, following which the resulting full-length primer extension products can be resolved and measured, and such measurements compared.

In other exemplary embodiments, the processivity of a given polymerase can be measured using any suitable assay known in the art, including but not limited to the assays described in Von Hippel, P. H., Faireld, F. R. and Dolejsi, M. K., *On the processivity of polymerases*, Ann. NY Acad. Sci., 726:118-131 (1994); Bambara, R. A., Uyemura, D. and Choi, T., *On the processive mechanism of Escherichia coli DNA polymerase I. Quantitative assessment of processivity*, J. Biol. Chem., 253:413-423 (1978); Das, S. K. and Fujimura, R. K., *Processiveness of DNA polymerases. A comparative study using a simple procedure*, J. Biol. Chem., 254: 1227-1232 (1979); Nasir, M. S. and Jolley, M. E., *Fluorescence polarization: An Analytical Tool for Immunoassay and Drug Discovery*, Combinational Chemistry and High Throughput Screening, 2:177-190 (1999); Mestas, S. P., Sholders, A. J., and Peersen, O. B., *A Fluorescence Polarization Based Screening Assay for Nucleic Acid Polymerase Elongation Activity*, Anal. Biochem., 365:194-200 (2007); Nikiforov, T. T., *Fluorogenic polymerase, endonuclease, and ligase assays based on DNA substrates labeled with a single fluorophore*, Analytical Biochemistry 412: 229-236; and Yan Wang, Dennis E. Prosen, Li Mei, John C. Sullivan, Michael Finney and Peter B. Vander Horn, Nucleic Acids Research, 32(3):1197-1207 (2004).

The terms "read length" or "read-length" and their variants, as used herein, refer to the number of nucleotides that are polymerized (e.g., incorporated into a nucleic acid strand) often in a template-dependent manner by a polymerase, prior to dissociation from the template. In some embodiments, a polymerase that dissociates from the template after five incorporations will typically provide a sequence having a read length of 5 nucleotides, while a polymerase that dissociates from the template after 500 nucleotide incorporations will typically provide a sequence having a read length of about 500 nucleotides. While the actual or absolute processivity of a given polymerase (or the actual read length of polymerization products produced by the polymerase) can vary from reaction to reaction (or even within a single reaction mixture wherein the polymerase produces different products having different read lengths), the polymerase can be characterized by the average processivity (or average read length of polymerization products) observed under a defined set of reaction conditions. Accordingly, the "error-free read length" comprises the number of nucleotides that are consecutively and contiguously incorporated by a polymerase without error (i.e., without mismatch and/or deviation from an established and predictable set of base pairing rules) into the newly synthesized nucleic acid strand.

In some embodiments, the disclosure relates generally to compositions, methods, systems, apparatuses and kits comprising modified polymerases that are characterized by increased processivity, read length (including error-free read length) and/or accuracy as compared to their unmodified counterparts, as well as to methods for making and using such modified polymerases in a wide range of biological and chemical reactions such as nucleotide polymerization, primer extension, generation of nucleic acid libraries and nucleic acid sequencing reactions. In some embodiments, the modified polymerases include one or more amino acid mutations (e.g., amino acid substitutions) relative to their corresponding unmodified counterparts. In some embodiments, the modified polymerases are capable of incorporating a blocked or 2' or 3' or 4' reversibly blocked nucleotide.

In some embodiments, the modified polymerase can amplify and/or sequence a nucleic acid molecule in the presence of a high ionic strength solution. In some embodiments, a modified polymerase is capable of amplifying (and/or sequencing) a nucleic acid molecule in the presence of a high ionic strength solution to a greater extent (for example as measured by processivity) than a reference polymerase lacking one or more of the same amino acid substitutions under identical conditions. In some embodiments, the disclosure generally relates to a modified polymerase or a biologically active fragment thereof that can perform nucleotide polymerization or nucleotide incorporation of a 2' or 3' or 4' reversibly blocked nucleotide in the presence of elevated salt conditions as compared to a reference polymerase.

In some embodiments, the disclosure relates generally to methods, compositions, systems and kits comprising the use of such modified polymerases in nucleotide polymerization reactions, including nucleotide polymerization reactions wherein sequence information is obtained from a nucleic acid molecule. In some embodiments, the disclosure relates generally to methods, compositions, systems and kits comprising the use of such modified polymerases in clonal amplification reactions, including nucleic acid library synthesis. In some embodiments, the disclosure relates to methods for using such modified polymerases in ion-based nucleic acid sequencing reactions, wherein sequence information is obtained from a template nucleic acid using an ion-based sequencing system. In some embodiments, the disclosure relates generally to compositions, methods, systems, kits and apparatuses for carrying out a plurality of DNA sequencing reactions (e.g., ion-based sequencing reactions) using a large-scale array of electronic sensors, for example field effect transistors ("FETs").

In some embodiments, the processivity of a given set of polymerases (including any of the reference or modified polymerases described herein) can be measured in an ion based sequencing reaction run; optionally, the processivity of a set of polymerases can be compared with each other to determine whether a given amino acid substitution increases or decreases the processivity relative to a reference or unmodified polymerase. In some embodiments, the processivity of the polymerases can be measured using any ion-based sequencing apparatus supplied by Ion Torrent Technologies (Ion Torrent Systems, Life Technologies, Carlsbad, Calif.), including for example the Ion Torrent PGM™ Sequencer (Ion Torrent Systems, Life Technologies, Part No. 4462917), optionally using the sequencing protocols and reagents provided by Ion Torrent Systems.

In some embodiments, the disclosure relates generally to an isolated modified polymerase including at least one amino acid substitution relative to a reference polymerase and providing an increased average read length of primer extension products in a primer extension reaction using the modified polymerase, relative to the average read length of primer extension products obtained using the reference polymerase. In some embodiments, the isolated modified polymerase provides an increased average error-free read length of primer extension products in a primer extension reaction using the modified polymerase, relative to the average error-free read length of primer extension products obtained using the corresponding unmodified polymerase. Optionally, the modified polymerase includes two or more amino acid substitutions relative to the unmodified polymerase. In some embodiments, the modified polymerase comprises an amino acid substitution that allows for or improves incorporation of a 2' or 3' or 4' reversibly blocked nucleotide.

In some embodiments, the disclosure relates generally to methods for performing a nucleotide polymerization reaction, comprising contacting a modified polymerase with a nucleic acid template in the presence of one or more 2' or 3' or 4' reversibly blocked nucleotides; and polymerizing at least one of the one or more 2' or 3' or 4' reversibly blocked nucleotides using the modified polymerase. The polymerizing optionally further includes polymerizing the at least one 2' or 3' or 4' reversibly blocked nucleotide in a template-dependent fashion. In some embodiments, the modified polymerase includes one or more amino acid substitutions relative to a reference polymerase that does not include the one or more amino acid substitutions. In some embodiments, the method further includes hybridizing a primer to the template prior to, during, or after the contacting. The polymerizing can include polymerizing the at least one 2' or 3' or 4' reversibly blocked nucleotide onto an end of the primer using the modified polymerase or a biologically active fragment thereof.

In some embodiments, the modified polymerase, the reference polymerase, or both the modified and reference polymerase is a DNA polymerase. The DNA polymerase can include, without limitation, a bacterial DNA polymerase, prokaryotic DNA polymerase, eukaryotic DNA polymerase, archaeal DNA polymerase, viral DNA polymerase or phage DNA polymerase.

In some embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, *Bacillus* DNA polymerase I, Taq DNA polymerase, Platinum Taq DNA polymerase series, Omni Klen Taq DNA polymerase series, Klen Taq DNA polymerase series, T7 DNA polymerase, T5 DNA polymerase and Tth DNA polymerase. In some embodiments, the DNA polymerase is Bst DNA polymerase. In other embodiments, the DNA polymerase is *E. coli* DNA polymerase I. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfu turbo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator™ polymerase, phage Phi29 polymerase, T4 DNA polymerase, RB69 DNA polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 which is incorporated by reference herein.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

Suitable bacterial DNA polymerases include without limitation *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase, *Bacillus stearothermophilus* (Bst) DNA polymerase and *Sulfolobus solfataricus* (Sso) DNA polymerase.

Suitable eukaryotic DNA polymerases include without limitation the DNA polymerases α, δ, ε, η, ζ, γ, β, σ, λ, μ, ι, and κ, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as Φ29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase, PRD1 polymerase; Nf polymerase; M2Y polymerase; SF5 polymerase; f1 DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA 1; *Pyrodictium occultum* DNA polymerase; *Methanococcus voltae* DNA polymerase; *Methanococcus thermoautotrophicum* DNA polymerase; *Methanococcus jannaschii* DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

In some embodiments, the modified polymerase is an RNA polymerase. Suitable RNA polymerases include, without limitation, T3, T5, T7, and SP6 RNA polymerases. In some embodiments, the polymerase is a reverse transcriptase. Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., Carlsbad, Calif.) and telomerases.

In some embodiments, the modified polymerase is derived from a known DNA polymerase. The DNA polymerases have been classified into seven different families, based upon both amino acid sequence comparisons and three-dimensional structure analyses. The DNA polymerase I (pol I) or type A polymerase family includes the repair polymerases *E. coli* DNA pol I, *Thermus aquaticus* pol I, and *Bacillus stearothermophilus* pol I, replicative DNA polymerases from some bacteriophages (T3, T5 and T7) and eukaryotic mitochondrial DNA polymerases. The DNA polymerase α (pol α) or type B polymerase family includes all eukaryotic replicating DNA polymerases as well as archaebacterial DNA polymerases, viral DNA polymerases, DNA polymerases encoded in mitochondrial plasmids of various fungi and plants, and the polymerases from bacteriophages T4 and RB69. Family C polymerases are the primary bacterial chromosome replicative enzymes. These are sometimes considered a subset of family Y, which contains the eukaryotic polymerase pol β, as well as other eukaryotic polymerases such as pol σ, pol λ, pol μ, and terminal deoxynucleotidyl transferase (TdT). Family D polymerases are all found in the Euryarchaeota subdomain of Archaea and are thought to be replicative polymerases. The family Y polymerases are called translesion synthesis (TLS) polymerases due to their ability to replicate through damaged DNA. They are also known as error-prone polymerases since they have a low fidelity on undamaged templates. This family includes Pol η, Polζ, Pol ι (iota), Pol κ (kappa), and Rev1, and Pol IV and PolV from *E. coli*. Finally, the reverse transcriptase family includes reverse transcriptases from retroviruses and eukaryotic polymerases, usually restricted to telomerases. These polymerases use an RNA template to synthesize the DNA strand, and are also known as RNA-dependent DNA polymerases.

In some embodiments, a modified polymerase or biologically active fragment thereof can be prepared using any suitable method or assay known to one of skill in the art. In some embodiments, any suitable method of protein engineering can be used to obtain a modified polymerase or biologically active fragment thereof encompassed by the disclosure. For example, site-directed mutagenesis is a technique that can be used to introduce one or more known or random mutations within a DNA construct. The introduction of the one or more amino acid mutations can be verified for example, against a standard or reference polymerase or via nucleic acid sequencing to confirm the corresponding amino acid sequence. Once verified, the construct containing the one or more of the amino acid mutations can be transformed into bacterial cells and expressed.

Typically, colonies containing mutant expression constructs are inoculated in media, induced, and grown to a desired optical density before collection (often via centrifugation) and purification of the supernatant. It will be readily apparent to the skilled artisan that the supernatant can be purified by any suitable means. Typically, a column for analytical or preparative protein purification is selected. In some embodiments, a modified polymerase or biologically active fragment thereof prepared using the methods can be purified, without limitation, over a heparin column essentially according to the manufacturer's instructions.

Once purified, the modified polymerase or biologically active fragment thereof can be assessed using any suitable method for various polymerase activities. In some embodiments, the polymerase activity being assessed will depend on the application of interest. For example a polymerase used to amplify or sequence a nucleic acid molecule of about 400 bp in length may include polymerase activities such as increased processivity relative to a reference polymerase lacking the one or more amino acid modifications.

In some embodiments, the modified polymerase or a biologically active fragment thereof, includes one or more amino acid mutations that are located outside the catalytic domain (also referred to herein as the DNA binding cleft) of the polymerase. The catalytic domains of the A family DNA polymerases, B family DNA polymerases and reverse transcriptases, as well as the RNA-dependent RNA polymerases are well known; all share a common overall structure and catalytic mechanism. The catalytic domains of all these polymerases have a shape that has been compared to a right hand and consists of "palm", "thumb" and "finger" domains. The palm domain typically contains the catalytic site for the phosphoryl transfer reaction. The thumb is thought to play a role positioning the duplex DNA and in processivity and translocation. The fingers interact with the incoming nucleotide as well as the template base with which it is paired. The palm domains are homologous in the A, B and RT families, but the arrangements of the fingers and thumb are different.

The thumb domains of the different polymerase families do share common features, containing parallel or anti-parallel α-helices, with at least one α-helix interacting with the minor groove of the primer-template complex. The fingers domain also conserves an α-helix positioned at the blunt end of the primer-template complex. This helix contains highly conserved side chains (the B motif).

Three conserved motifs, A, B, and C have been identified for the A family polymerases. The A and C motifs are typically conserved in both the B family polymerases and the RT polymerases. (Delarue et al., Protein Engineering 3: 461-467 (1990)). In some embodiments, the polymerase optionally comprises any A family polymerase, or biologically active fragment, mutant, variant or truncation thereof, wherein the linking moiety is linked to any amino acid residue of the A family polymerase, or biologically active fragment mutant, variant or truncation thereof, that is situated outside the A, B or C motifs. In some embodiments, the linking moiety is linked to any amino acid residue of the A family polymerase, or biologically active fragment, that is situated outside the A motif, the B motif or the C motif. The A and C motifs typically form part of the palm domain, and each motif typically contains a strictly conserved aspartic acid residue, which are involved in the catalytic mechanism common to all the DNA polymerases. DNA synthesis can be mediated by transfer of a phosphoryl group from the incoming nucleotide to the 3' OH of the DNA, releasing a polyphosphate moiety and forming a new DNA phosphodiester bond. This reaction is typically catalyzed by a mechanism involving two metal ions, normally $Mg^{2+}$, and the two conserved aspartic acid residues.

In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside the A, B or C motifs. In some embodiments, the linking moiety is linked to any amino acid residue of the B family polymerase, or biologically active fragment, that is situated outside the A motif, the B motif or the C motif. In some embodiments, the B family polymerases contain six conserved motifs, of which regions I and II correspond to the A and C motifs of the A family. Region III is involved in nucleotide binding and is functionally homologous to motif B. Regions I, II and III converge at the center of the active site from the palm (I), the fingers (II), and base of the thumb (III) to produce a contiguous conserved surface. Within these regions, a set of highly conserved residues form three chemically distinct clusters consisting of exposed aromatic residues, negatively charged residues, and positively charged residues, respectively. For example, in the replication polymerase of the bacteriophage RB69, these three clusters corresponds to the following amino acid residues: Y416, Y567, and Y391 (exposed aromatic residues), D621, D623, D411, D684, and E686 (negatively charged residues), and K560, R482, and K486 (positively charged residues). See Wang et al, Cell 89: 1087-1099 (1997). These three clusters typically encompass the region in which the primer terminus and the incoming nucleotide would be expected to bind. In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside one or more of these conserved amino acid clusters or motifs. In some embodiments, the linking moiety is linked to any amino acid residue of the B family polymerase, or biologically active fragment, mutant, variant or truncation thereof that is situated outside any of these conserved amino acid clusters or motifs.

In some embodiments, in addition to the polymerase domains, the modified polymerase can include one or more additional functional domains, including domains required for 3'→5' (reverse) exonuclease activity that mediates proofreading of the newly synthesized DNA strand, or for 5'→3' (forward) exonuclease activity that mediates nick translation during DNA repair, or for FLAP endonuclease activity. In some embodiments, the modified polymerase has strand-displacing activity, and can catalyze nucleic acid synthesis by polymerizing nucleotides into the 3' end of a nick within a double stranded nucleic acid template while simultaneously displacing the nucleic acid located downstream of the nick.

The 3' to 5' exonuclease proofreading domains of both A and B family DNA polymerases contain three conserved motifs, called Exo I, Exo II and Exo III, each of which contains an invariant aspartic acid residue essential for metal binding and exonuclease function. Alterations of these conserved aspartic acid residues result in proteins which retain polymerase activity, but are deficient in exonuclease activity (Hall et al., J. Gen. Virol. 76: 2999-3008 (1995)). Conserved motifs in the 5' to 3' exonuclease domains and amino acid alterations that affect exonuclease activity have also been identified (U.S. Pat. No. 5,466,591).

In some embodiments, the modified polymerase is derived from Taq DNA polymerase, which is an A family DNA polymerase derived from the thermophilic bacterium *Thermus aquaticus*. It is best known for its use in the polymerase chain reaction. Taq polymerase lacks a proofreading activity, and thus has a relatively low replication fidelity (Kim et al., Nature 376: 612-616 (2002).

In some embodiments, the modified polymerase is derived from the T7 DNA polymerase of bacteriophage T7, which is an A family DNA polymerase that consists of a 1:1 complex of the viral T7 gene 5 protein (80 k Da) and the *E. coli* thioredoxin (12 k Da). T7 DNA polymerase lacks a 5'→3' exonuclease domain, but the 3'→5' exonuclease activity is approximately 1000-fold greater than that of *E. coli* Klenow fragment. The exonuclease activity appears to be responsible for the high fidelity of this enzyme and prevents strand displacement synthesis. This polymerase typically exhibits high levels of processivity.

In some embodiments, the modified polymerase is derived from KOD DNA polymerase, which is a B family DNA polymerase derived from *Thermococcus kodakaraensis*. KOD polymerase is a thermostable DNA polymerase with high fidelity and processivity.

In some embodiments, the modified polymerase is derived from the Therminator™ DNA polymerase, which is also a B family DNA polymerase. Therminator™ is an A485L point mutation of the DNA polymerase from *Thermococcus* species 9oN-7 (Ichida et al., Nucleic Acids Res. 33: 5214-5222 (2005)). Therminator™ polymerase has an enhanced ability to incorporate modified substrates such as dideoxynucleotides, ribonucleotides, acyclonucleotides and reversibly blocked nucleotides.

In some embodiments, the modified polymerase is derived from a Phi29 polymerase or a Phi29-type polymerase, for example a polymerase derived from the bacteriophage B103. The Phi29 and B103 DNA polymerases are B family polymerases from related bacteriophages. In addition to the A, B and C motifs, the Phi29 family of DNA polymerases contain an additional conserved motif, KXY in region Y (Blanco et al., J. Biol. Chem. 268: 16763-16770 (1993). Mutations to Phi29 and B103 polymerases that affect polymerase activity and nucleotide binding affinity are described in U.S. Patent Publication No. 20110014612 and its priority documents U.S. Provisional Application Nos. 61/307,356; 61/299,917; 61/299,919; 61/293,616; 61/293, 618; 61/289,388; 61/263,974; 61/245,457; 61/242,771; 61/184,770; and 61/164,324, herein incorporated by reference in their entireties.

In some embodiments, the modified polymerase is derived from the reverse transcriptase from human immunodeficiency virus type 1 (HIV-1), which is a heterodimer consisting of one 66-kDa and one 51-kDa subunit. The p66 subunit contains both a polymerase and an RNase H domain; proteolytic cleavage of p66 removes the RNase H domain to yield the p51 subunit (Wang et al., PNAS 91:7242-7246 (1994)). The structure of the HIV-1 reverse transcriptase show multiple interactions between the 2'-OH groups of the RNA template and the reverse transcriptase. Residues Ser280 and Arg284 of helix I in the p66 thumb are involved in the RNA-RT interactions, as well as residues Glu89 and Gln91 of the template grip in the p66 palm. The p51 subunit also plays a role in the interactions between the RNA-DNA duplex and the RT, with residues Lys395, Glu396, Lys22 and Lys390 of the p51 subunit also interacting with the DNA: RNA duplex (Kohlstaedt et al, Science 256: 1783-1790 (1992) and Safarianos et al, The EMBO Journal 20:1449-1461 (2001)).

In some embodiments, the modified polymerase is derived from the Bst DNA polymerase of *Bacillus stearothermophilus*. The large fragment of the naturally occurring Bst DNA polymerase is equivalent to the Klenow fragment of *E. coli* Pol I, retaining the polymerase and proofreading exonuclease activities while lacking the 5' to 3' exonuclease activity. In some embodiments, the polymerase derived from Bst DNA polymerase can lack 3' to 5' exonuclease activity. As used herein, the term "Bst DNA polymerase" may refer to a full-length protein, while "Bst large fragment" refers to the large fragment of Bst, which is known in the art.

In some embodiments, the modified polymerase consists of or comprises an isolated variant of a Bst large fragment having or comprising the amino acid sequence of SEQ ID NO: 1:

```
                                              (SEQ ID NO: 1)
        10         20         30         40
MAKMAFTLAD RVTEEMLADK AALVVEVVEE NYHDAPIVGI 50         60         70         80
AVVNERGRFF LRPETALADP QFVAWLGDET KKKSMFDSKR 90        100        110        120
AAVALKWKGI ELCGVSFDLL LAAYLLDPAQ GVDDVAAAAK 130        140        150        160
MKQYEAVRPD EAVYGKGAKR AVPDEPVLAE HLVRKAAAIW 170        180        190        200
ELERPFLDEL RRNEQDRLLV ELEQPLSSIL AEMEFAGVKV 210        220        230        240
DTKRLEQMGK ELAEQLGTVE QRIYELAGQE FNINSPKQLG 250        260        270        280
VILFEKLQLP VLKKTKTGYS TSADVLEKLA PYHEIVENIL 290        300        310        320
HYRQLGKLQS TYIEGLLKVV RPDTKKVHTI FNQALTQTGR 330        340        350        360
LSSTEPNLQN IPIRLEEGRK IRQAFVPSES DWLIFAADYS 370        380        390        400
QIELRVLAHI AEDDNLMEAF RRDLDIHTKT AMDIFQVSED 410        420        430        440
EVTPNMRRQA KAVNFGIVYG ISDYGLAQNL NISRKEAAEF 450        460        470        480
IERYFQSFPG VKRYMENIVQ EAKQKGYVTT LLHRRRYLPD 490        500        510        520
ITSRNFNVRS FAERMAMNTP IQGSAADIIK KAMIDLNARL 530        540        550
KEERLQAHLL LQVHDELILE APKEEMERLC RLVPEVMEQA 560                   570             580
VTLRVPLKVD YRYGSTWYDA K
```

In some embodiments, SEQ ID NO: 1 includes three amino acid substitutions relative to wild-type, Bst large fragment of Bst DNA polymerase namely: His46Arg (H46R), Glu446Gln (E446Q), and His572Arg (H572R).

In some embodiments, the reference polymerase comprises a Bst DNA polymerase having, or comprising, the amino acid sequence of SEQ ID NO: 1 and the modified polymerase further includes one or more amino acid modifications (e.g., amino acid substitutions, deletions, additions or chemical modifications) relative to the reference polymerase (e.g., wild-type Bst large fragment), wherein the modified polymerase is capable of incorporating at least one 2' or 3' or 4' reversibly blocked nucleotide during a polymerization reaction.

In some embodiments, the modified polymerase is derived from any one of the Bst DNA polymerases described in U.S. published Application Nos. 2015/0260680, filed May 28, 2015, 2015/0368626, filed Jun. 29, 2015, or 2015/0094211, filed Sep. 30, 2014, all of which are herein incorporated by reference in their entireties. In some embodiments, the modified polymerase is derived from any one of the Bst DNA polymerases described in U.S. application Ser. No. 14/970,818, filed Dec. 16, 2015, or 62/235,616, filed Oct. 1, 2015, which are herein incorporated by reference in their entireties.

In some embodiments, the modified polymerase is a Taq DNA polymerase that includes one or more amino acid substitutions (as compared to the reference polymerase) that allows incorporation of a blocked nucleotide or a 2' or 3' or 4' reversibly blocked nucleotide during a polymerization reaction. In some embodiments, the polymerase is a Taq DNA polymerase commercially available as Platinum Taq High Fidelity DNA polymerase (Life Technologies, CA), that includes one or more amino acid mutations as compared to the reference polymerase (e.g., Platinum Taq High Fidelity DNA polymerase).

In some embodiments, the modified polymerase or any biologically active fragment of a polymerase can include one or more biotin moieties. As used herein, the terms "biotin" and "biotin moiety" and their variants comprise biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like, as well as any biotin variants that can specifically bind to an avidin moiety. The terms "avidin" and "avidin moiety" and their variants, as used herein, comprise the native egg-white glycoprotein avidin, as well as any derivatives, analogs and other non-native forms of avidin, which can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety. As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-14}$ to $10^{-15}$ mol/L. Typically, such binding occurs via non-covalent interactions.

In some embodiments, the modified polymerase or any biologically active fragment of a polymerase can include one or more modified or substituted amino acids relative to the reference polymerase, and can further include a biotin moiety that is linked to at least one of the one or more modified or substituted amino acids. The biotin moiety can be linked to the modified polymerase using any suitable linking method. In some embodiments, the modified polymerase includes one or more cysteine replacement substitutions, and the linking moiety includes a biotin moiety that is linked to at least one of the one or more cysteine replacement substitutions.

In some embodiments, the disclosure relates generally to a method for incorporating at least one 2' or 3' or 4' reversibly blocked nucleotide into a primer, comprising contacting a nucleic acid complex including a template nucleic acid with a primer and a modified polymerase in the presence of one or more 2' or 3' or 4' reversibly blocked nucleotides, and incorporating at least one of the one or more 2' or 3' or 4' reversibly blocked nucleotides into the primer, optionally in a template-dependent fashion, using said modified polymerase.

Methods for nucleotide incorporation are well known in the art and typically comprise use of a polymerase reaction mixture in which the polymerase is contacted with the template nucleic acid under nucleotide incorporation conditions. When the nucleotide incorporation reaction comprises polymerization of nucleotides onto the end of a primer, the process is typically referred to as "primer extension." Typically but not necessarily such nucleotide incorporation occurs in a template-dependent fashion. Primer extension and other nucleotide incorporation assays are typically performed by contacting the template nucleic acid with a polymerase in the presence of nucleotides in an aqueous solution under nucleotide incorporation conditions. In some embodiments, the nucleotide incorporation reaction can include a primer, which can optionally be hybridized to the template to form a primer-template duplex. Typical nucleotide incorporation conditions are achieved once the template, polymerase, nucleotides and optionally primer are mixed with each other in a suitable aqueous formulation, thereby forming a nucleotide incorporation reaction mixture (or primer extension mixture). The aqueous formulation can optionally include divalent cations and/or salts, particularly $Mg^{++}$ and/or $Ca^{++}$ ions. The aqueous formulation can optionally include divalent anions and/or salts, particularly $SO_4^{2-}$. Typical nucleotide incorporation conditions have included well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. In some embodiments, the reagents or buffers can include a source of detergent such as Triton and/or Tween. Most polymerases exhibit some levels of nucleotide incorporation activity over pH range of about 5.0 to about 9.5, more typically between about pH 7 and about pH 9, sometimes between about pH 6 to about pH 8, and sometimes between 7 and 8. The buffer may include chelating agents such as EDTA and EGTA, and the like. Although in some embodiments, nucleotide incorporation reactions may include buffering agents, such as Tris, Tricine, HEPES, MOPS, ACES, or MES, which can provide a pH range of about 5.0 to about 9.5, such buffering agents can optionally be reduced or eliminated when performing ion-based reactions requiring detection of ion byproducts.

Methods of performing nucleic acid synthesis are well known and extensively practiced in the art and references teaching a wide range of nucleic acid synthesis techniques are readily available. Some exemplary teachings regarding the performance of nucleic acid synthesis (including, for example, template-dependent nucleotide incorporation, as well as primer extension methods, as well as incorporation of reversibly blocked nucleotides) can be found, for example, in Kim et al., Nature 376: 612-616 (2002); Ichida et al., Nucleic Acids Res. 33: 5214-5222 (2005); Pandey et al., European Journal of Biochemistry, 214:59-65 (1993); Blanco et al., J. Biol. Chem. 268: 16763-16770 (1993); U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617; U.S. patent application Ser. No. 12/748,359, now published as U.S. Patent Publication No. 20110014612; and Chen et al., Genomics Proteomics Bioinformatics 11 (2013) 34-40. Given the ample teaching of primer extension and other nucleotide incorporation reactions in the art, suitable reaction conditions for using the modified polymerases of the disclosure to perform nucleotide incorporation, including incorporation of blocked or reversibly blocked nucleotides will be readily apparent to the skilled artisan.

In some embodiments, the disclosed modified polymerase compositions, (as well as related methods, systems, apparatuses and kits) can be used to obtain sequence information from a nucleic acid molecule. Many methods of obtaining sequence information from a nucleic acid molecule are known in the art, and it will be readily appreciated that all such methods are within the scope of the present disclosure. Suitable methods of sequencing using the disclosed modified polymerases include without limitation: Sanger sequencing, ligation-based sequencing (also known as sequencing by hybridization) and sequencing by synthesis. Sequencing by synthesis using the modified polymerases of the disclosure will typically involve detecting the order and identity of nucleotide incorporation when nucleotides are polymerized in a template-dependent fashion by the modified polymerase. Some exemplary methods of sequence-by-synthesis using labeled nucleotides include single molecule sequencing (see, e.g., U.S. Pat. Nos. 7,329,492 and 7,033,764), which typically involve the use of labeled nucleotides to detecting nucleotide incorporation. In some embodiments, the disclosed polymerase compositions (and related methods, kits, systems and apparatuses) can be used to obtain sequence information for whole genome sequencing, amplicon sequencing, targeted re-sequencing, single molecule sequencing, multiplex sequencing, and paired end sequencing applications. In one embodiment, the disclosed modified polymerase compositions, (as well as related methods, systems, apparatuses and kits) can be used to obtain sequence information from a nucleic acid molecule, wherein the sequence information includes determining the identification of a 2' or 3' or 4' reversibly blocked nucleotide into the nucleic acid molecule.

In some embodiments, the disclosed modified polymerase compositions as well as related methods, systems, apparatuses and kits, can be used to amplify nucleic acid molecules. In some embodiments, a nucleic acid molecule can be amplified using a modified polymerase and one or more different 2' or 3' or 4' reversibly blocked nucleotides in the presence of a primer under suitable amplification conditions.

In some embodiments, the disclosed modified polymerase compositions in combination with at least one 2' or 3' or 4' reversibly blocked nucleotides (as well as related methods, systems, apparatuses and kits), can be used to generate nucleic acid libraries. In some embodiments, the disclosed modified polymerase compositions in combination with at least one 2' or 3' or 4' reversibly blocked nucleotide can be used to generate nucleic acid libraries for a variety of downstream processes. Many methods for generating nucleic acid libraries are known in the art, and it will be readily appreciated that all such methods are within the scope of the present disclosure.

In some embodiments, methods for generating nucleic acid libraries using one or more of modified polymerases in combination with at least one type of 2' or 3' or 4' reversibly blocked nucleotide according to the disclosure can include the generation of a nucleic acid library of 50, 100, 200, 300, 400, 500, 600 or more base pairs in length. In some embodiments, the nucleic acid template to which the modified polymerase can perform nucleotide incorporation can be attached, linked or bound to a support, such as a solid support. In some embodiments, the support can include a planar support such as slide or flow cell. In some embodiments, the support can include a particle, such as an Ion Sphere™ particle.

In some embodiments, the disclosure relates generally to a method for generating a nucleic acid library comprising contacting a nucleic acid template with a modified polymerase and a 2' or 3' or 4' reversibly terminated nucleotide under polymerizing conditions; thereby incorporating at least one 2' or 3' or 4' reversibly terminated nucleotide into the nucleic acid template to generate a nucleic acid library. In some embodiments, the method can further include generating a nucleic acid library or sequencing a nucleic acid library in the presence of a high ionic strength solution. In some embodiments, the modified polymerase is capable of amplifying (and/or sequencing) a nucleic acid molecule in the presence of a high ionic strength solution to a greater capacity (for example as measured by processivity) than a reference polymerase lacking one or more of the same amino acid substitutions under identical conditions. Optionally, the method further includes repeating the addition of a 2' or 3' or 4' reversibly terminated nucleotide under polymerizing conditions to incorporate an additional 2' and/or 3' and/or 4' reversibly terminated nucleotide into the nucleic acid template to generate the nucleic acid library.

In some embodiments, the method can further include detecting a 2' or 3' or 4' reversibly terminated nucleotide incorporation by-product during the polymerization reaction. In some embodiments, the 2' or 3' or 4' reversibly terminated nucleotide incorporation by-product can include a hydrogen ion. In some embodiments, the method can further include determining the identity of the incorporated 2' or 3' or 4' reversibly terminated nucleotide in the nucleic acid library. In some embodiments, the method further includes determining the number of incorporated 2' or 3' or 4' reversibly terminated nucleotides in the nucleic acid library. In some embodiments, the detecting can further include sequencing the nucleic acid library.

In some embodiments, the disclosed modified polymerase compositions, (as well as related methods, systems, apparatuses and kits) can be used to detect nucleotide incorporation through the generation of by-product formation during the nucleotide incorporation event. Many methods of detecting nucleotide incorporation by-products are known in the art, and it will be readily appreciated that all such methods are within the scope of the present disclosure. Suitable methods of nucleotide by-product detection include without limitation, detection of hydrogen ion, inorganic phosphate, inorganic pyrophosphate, and the like. Several of these by-product detection methods typically involve template-dependent nucleotide incorporation.

In a typical embodiment of ion-based nucleic acid sequencing (such as Ion Torrent™ sequencing, sold by ThermoFisher Scientific), natural nucleotide incorporation is detected by detecting the presence and/or concentration of hydrogen ions generated by polymerase-catalyzed nucleic acid synthesis reactions, including for example primer extension reactions. In one embodiment, templates that are operably bound to a primer and a polymerase and that are situated within reaction chambers (such as the microwells), are subjected to repeated cycles of polymerase-catalyzed nucleotide addition to the primer ("adding step") followed by washing ("washing step"). In such embodiments, the templates may be attached as clonal populations to a solid support, such as a microparticle, bead, and said clonal populations are loaded into reaction chambers. As recited here, "operably bound" means that the primer is annealed to the template so that the primer can be extended by the polymerase and that the polymerase is bound to such primer-template duplex, or in close proximity thereof, so that primer extension takes place whenever the correct base-pairing natural nucleotides are supplied.

In each adding step of the cycle, the polymerase extends the primer by incorporating a natural nucleotide in a template-dependent fashion, such that the natural nucleotide is incorporated only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. In some embodiments, the production of hydrogen ions is proportional to (e.g., monotonically related) to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released. In some embodiments, after each step of adding a nucleotide, a washing step is performed, in which an unbuffered wash solution at a predetermined pH is used to remove the natural nucleotide of the previous step in order to prevent nucleotide misincorporations in later cycles. In some embodiments, after each step of adding a natural nucleotide, an additional step may be performed wherein the reaction chambers are treated with a nucleotide-destroying agent, such as apyrase, to eliminate any residual natural nucleotides remaining in the chamber, thereby minimizing the probability of spurious extensions in subsequent cycles. In some embodiments, the treatment may be included as part of the washing step itself.

In one exemplary embodiment, the disclosure relates generally to a method for obtaining sequence information from a nucleic acid template, comprising (a) providing a reaction mixture including a template nucleic acid hybridized to a sequencing primer and bound to a modified polymerase, wherein the modified polymerase comprises one or more amino acid substitutions as compared to a reference or unmodified polymerase; (b) contacting the template nucleic acid with a 2' or 3' or 4' reversibly blocked nucleotide, wherein the contacting includes incorporating the 2' or 3' or 4' reversibly blocked nucleotide into the sequencing primer and generating a sequencing byproduct if the 2' or 3' or 4' reversibly blocked nucleotide is complementary to a corresponding nucleotide in the template nucleic acid; and (c) detecting the presence of the sequencing byproduct in the reaction mixture, thereby determining whether a 2' or 3' or 4' reversibly blocked nucleotide incorporation has occurred.

In some embodiments, the method can further include repeating the contacting and detecting steps at least twice. In some embodiments, detecting the presence of the sequencing byproduct includes contacting the reaction mixture with a sensor capable of sensing the presence of the sequencing byproduct. The sensor can include a field effect transistor, for example a chemFET or an ISFET. In some embodiments, the sequencing byproduct includes a hydrogen ion, a dye-linked moiety, a polyphosphate, a pyrophosphate or a phosphate moiety, and detecting the presence of the sequencing byproduct includes using an ISFET to detect the sequencing byproduct. In some embodiments, detecting the sequencing byproduct includes detecting a hydrogen ion using the ISFET.

In some embodiments, the modified polymerase incorporates at least one 3'OH reversibly blocked nucleotide during polymerization and exhibits increased read length and/or processivity relative to an unmodified form of the polymerase under otherwise similar or identical reaction conditions.

In some embodiments, the modified polymerase incorporates at least one 2' reversibly blocked nucleotide during polymerization and exhibits increased read length and/or processivity relative to an unmodified form of the polymerase under otherwise similar or identical reaction conditions.

In a further embodiment, the disclosure relates generally to a method of detecting nucleotide incorporation, comprising (a) performing a nucleotide incorporation using a modified polymerase and at least one 2' or 3' or 4' reversibly blocked nucleotide thereby generating one or more byproducts of the nucleotide incorporation; and (b) detecting the presence of at least one of the one or more byproducts of the nucleotide incorporation, thereby detecting the 2' or 3' or 4' reversibly blocked nucleotide incorporation.

In some embodiments, the disclosure relates generally to a method of detecting a change in ion concentration during a nucleotide polymerization reaction, comprising (a) performing a nucleotide polymerization reaction using a modified polymerase and at least one 2' or 3' or 4' reversibly blocked nucleotide, wherein the concentration of at least one type of ion changes during the course of the nucleotide polymerization reaction; and (b) detecting a signal indicating the change in concentration of the at least one type of ion. In some embodiments, the at least type of ion includes a hydrogen ion, a polyphosphate, a pyrophosphate or a phosphate moiety, and detecting the change in concentration of the at least one type of ion includes using an ISFET to detect the at least one type of ion. In some embodiments, the at least one type of ion includes a hydrogen ion, and detecting the presence of the at least one type of ion includes detecting the hydrogen ion using an ISFET.

In some embodiments, the disclosure relates generally to a method for performing a nucleotide polymerization reaction, comprising contacting a modified polymerase or a biologically active fragment thereof with a nucleic acid template in the presence of one or more 2' or 3' or 4' reversibly blocked nucleotides, wherein the modified polymerase or the biologically active fragment thereof includes one or more amino acid substitutions relative to a reference polymerase lacking the corresponding amino acid substitutions, and wherein the modified polymerase has improved processivity relative to the reference polymerase; and polymerizing at least one of the one or more 2' or 3' or 4' reversibly blocked nucleotides using the modified polymerase or the biologically active fragment thereof.

In some embodiments, the method includes performing the nucleotide polymerization reaction in the presence of a high ionic strength solution. In some embodiments, the method further includes polymerizing at least one of the one or more 2' or 3' or 4' reversibly blocked nucleotides in a template-dependent fashion. In some embodiments, the method further includes hybridizing a primer to the nucleic acid template prior to, during or after the contacting, and wherein the polymerizing includes polymerizing at least one of the one or more 2' or 3' or 4' reversibly blocked nucleotides onto an end of the primer using the modified polymerase or the biologically active fragment thereof.

In some embodiments, the polymerizing is performed in the proximity of a sensor that is capable of detecting the polymerization of the at least one of the one or more 2' or 3' or 4' reversibly blocked nucleotides by the modified polymerase or the biologically active fragment thereof. In some embodiments, the method further includes detecting a signal indicating the polymerization of the at least one of the one or more 2' or 3' or 4' reversibly blocked nucleotides by the modified polymerase or the biologically active fragment thereof using a sensor. In some embodiments, the sensor is an ISFET.

In some embodiments, the disclosure relates generally to a method for performing nucleic acid amplification, comprising generating an amplification reaction mixture having a modified polymerase or a biologically active fragment thereof, a nucleic acid template, a primer, and one or more 2' or 3' or 4' reversibly blocked nucleotides, wherein the modified polymerase or the biologically active fragment thereof includes one or more amino acid modifications relative to a reference polymerase and has an increased mean read length relative to the reference polymerase; and subjecting the amplification reaction mixture to suitable amplifying conditions, wherein at least one of the one or more 2' or 3' or 4' reversibly blocked nucleotides is polymerized onto the end of the primer using the modified polymerase or the biologically active fragment thereof.

In some embodiments, the disclosure relates generally to a method of detecting nucleotide incorporation, comprising performing a nucleotide incorporation reaction using a modified polymerase or a biologically active fragment thereof in the presence of a nucleic acid template and one or more 2' or 3' or 4' reversibly blocked nucleotides; thereby generating one or more byproducts of the nucleotide incorporation; and detecting the presence of at least one of the one or more byproducts of the nucleotide incorporation, thereby detecting the nucleotide incorporation. In some embodiments, the method of nucleotide incorporation further includes determining the identity of the 2' or 3' or 4' reversibly blocked nucleotide incorporation. In some embodiments, the byproduct of the nucleotide incorporation is a hydrogen ion.

In some embodiments, the disclosure relates generally to a method for performing nucleic acid sequencing, comprising contacting a modified polymerase or a biologically active fragment thereof with a nucleic acid template in the presence of one or more 2' or 3' or 4' reversibly blocked nucleotides, wherein the modified polymerase or the biologically active fragment thereof includes one or more amino acid substitutions relative to a reference polymerase, and wherein the modified polymerase or the biologically active fragment thereof has increased processivity relative to the reference polymerase; and polymerizing at least one of the one or more 2' or 3' or 4' reversibly blocked nucleotides using the modified polymerase or the biologically active fragment thereof.

In some embodiments, the disclosure relates generally to methods, as well as related, systems, compositions, kits and apparatuses, for nucleotide incorporation with a sensor comprising an ISFET.

In some embodiments, any nucleic acid template can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. In some embodiments, a sequencing reaction can be conducted using at least one sequencing primer that can hybridize to any portion of the nucleic acid templates, including a nucleic acid adaptor or a target polynucleotide.

In some embodiments, any nucleic acid template can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, amplified target nucleic acids produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells. Exemplary embodiments of FET sensor arrays can be found in U.S. Pat. Nos. 7,948,015; 8,262,900; 8,776,573; 8,208,712, which are expressly incorporated herein by reference as if set forth in full.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 µm³ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing nucleic acid templates. In one exemplary embodiment, the disclosure relates generally to a method for obtaining sequence information from polynucleotides, comprising: incorporating a terminator nucleotide at the extendible end of the nucleic acid template; and detecting a non-optical signal indicating the nucleotide incorporation using a sensor that detects by-products (e.g., cleavage products) from the nucleotide incorporation reaction. In some embodiments, methods for sequencing comprise: (a) providing a surface including one or more reaction sites containing a polymerase and a nucleic acid template that has, or is hybridized to, an extendible end; (b) performing a first nucleotide flow by contacting one or more of the reaction sites with a first solution including one or more types of terminator nucleotide; (c) incorporating at least one type of a terminator nucleotide at the extendible end of the nucleic acid template contained within at least one of the reaction sites using the polymerase; and (d) detecting a non-optical signal indicating the nucleotide incorporation using a sensor that is attached or operatively linked to the at least one reaction site. Optionally, the sensor comprises a FET sensor. Optionally, at least one reaction site includes one or more FET sensors. Optionally, the methods for sequencing further include: de-blocking the terminator nucleotide which is incorporated. Optionally, the methods for sequencing further include: performing a second nucleotide flow by contacting one or more of the reaction sites with a second solution including one or more types of nucleotides, where the second solution contains one or more terminator nucleotides, one or more non-terminator nucleotides, or a mixture of both. Optionally, the methods for sequencing further include: incorporating at least a second nucleotide, where the second nucleotide is a terminator nucleotide or non-terminator nucleotide from the second solution. Optionally, the methods for sequencing further include: detecting a second non-optical signal indicating the second incorporated nucleotide using the sensor that is attached or operatively linked to the at least one reaction site.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: disposing the nucleic acid templates into a plurality of reaction chambers, wherein one or more of the reaction chambers are in contact with a field effect transistor (FET). Optionally, the method further includes contacting the nucleic acid templates which are disposed into one of the reaction chambers, with a polymerase thereby synthesizing a new nucleic acid strand by sequentially incorporating one or more nucleotides (e.g., terminator nucleotides) into a nucleic acid molecule (e.g., extendible end). Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

In some embodiments, the disclosed methods for detecting nucleotide incorporation and/or performing nucleic acid sequencing allow sequencing of nucleic acid templates at accuracies not provided by current sequencing methods. For example, in some embodiments, the disclosed methods include sequencing a stretch of contiguous nucleotides within a nucleic acid template with an error rate of less than 0.1%. Optionally, the error rate is less than 0.001%. In some embodiments, the error rate includes a mismatch error rate of less than 0.001%, optionally less than 0.0001%. In some embodiments, the error rate includes an in/del error rate of less than 0.1%, optionally less than 0.01%.

In some embodiments, the disclosure relates generally to methods (and related compositions, systems, kits and apparatuses) for nucleic acid sequencing, comprising identifying a series of contiguous nucleotides in a nucleic acid template according to any of the methods disclosed herein.

In some embodiments, the disclosure relates generally to methods (and related compositions, systems, apparatuses and kits) for nucleic acid sequencing, comprising: providing a surface including one or more reaction sites that contain a nucleic acid template having, or hybridized to, an extendible end and a polymerase; extending the extendible end by serially incorporating a plurality of nucleotides at the extendible end of at least one nucleic acid template using a polymerase, where at least one of the incorporated nucleotides is a reversible terminator nucleotide, and wherein the extending includes deblocking any incorporated reversible terminator nucleotide prior to next incorporation of a succeeding nucleotide; detecting at least two successive nucleotide incorporations and determining the identities of at least two successively incorporated nucleotides at a total error rate of less than 0.1%. In some embodiments, the total error rate is less than 0.01%. Optionally, the total error rate includes a mismatch error rate of less than 0.001%, optionally less than 0.0001%. Optionally, the total error rate includes an in/del error rate of less than 0.1%, optionally less than 0.01%

In some embodiments, the disclosure relates generally to systems for performing nucleotide incorporation. The system optionally includes a flow cell containing a surface. The surface optionally includes one or more reaction sites containing a polymerase and a nucleic acid template. The nucleic acid template optionally has, or is hybridized to, an extendible end. The system can include an inlet having one end connected to the flow cell. The inlet can include another end connected to a one or more reservoirs containing one or more types of nucleotide. The nucleotide can be a terminator nucleotide. In some embodiments, the system further includes a sensor configured to detect a non-optical signal indicating a nucleotide incorporation occurring at least one of the reaction sites.

What is claimed:

1. A method for detecting a nucleotide incorporation, comprising:
   a) providing a surface having a plurality of reaction sites, wherein each reaction site is attached or operatively linked to at least one sensor, and one or more of the reaction sites contain (i) a polymerase, (ii) a nucleic acid template and (iii) an extendible end;
   b) contacting the reaction sites with a first solution containing one or more types of terminator nucleotides, wherein the one or more types of terminator nucleotides comprise (1) a terminator moiety and (2) a tag moiety comprising a first binding partner that is capable of binding to a second binding partner that comprises a signal-generation moiety;
   c) incorporating at least one type of a terminator nucleotide at an extendible end and generating a non-extendible end having a terminator moiety, thereby generating a nucleotide incorporation product within one or more of the reaction sites;
   d) contacting the first binding partner of a tag moiety of the terminator nucleotide in the nucleotide incorporation product with a second binding partner comprising a signal-generation moiety thereby binding the first binding partner with the second binding partner; and
   e) detecting a non-optical signal generated by the signal-generation moiety of the second binding partner at one or more of the reaction sites using the sensors thereby detecting a nucleotide incorporation at the one or more reaction sites, wherein the signal is detected after incorporation of the nucleotide.

2. The method of claim 1, further comprising removing, cleaving or converting the terminator moiety or moieties and, optionally, the tag moiety or moieties, from the nucleotide incorporation product or products to generate an extendible end or ends.

3. The method of claim 2, further comprising:
   i) contacting one or more of the reaction sites with a subsequent solution containing one or more types of terminator nucleotides, wherein the one or more types of terminator nucleotides comprise (1) a terminator moiety and (2) a tag moiety comprising a first binding partner that is capable of binding to a second binding partner that comprises a signal-generation moiety;
   ii) incorporating at least one type of a terminator nucleotide at an extendible end and generating a non-extendible end having a terminator moiety, thereby generating a nucleotide incorporation product within one or more of the reaction sites;
   iii) contacting the first binding partner of a tag moiety of the terminator nucleotide in the nucleotide incorporation product with a second binding partner comprising a signal-generation moiety thereby binding the first binding partner with the second binding partner;
   iv) detecting a non-optical signal generated by the signal-generation moiety of the second binding partner at one or more of the reaction sites using the sensors thereby detecting a nucleotide incorporation at the one or more reaction sites; and
   v) removing, cleaving or converting the terminator moiety or moieties and, optionally, the tag moiety or moieties, from the nucleotide incorporation product or products to generate an extendible end or ends.

4. The method of claim 3, further comprising repeating steps i)-v) at least once.

5. The method of claim 1, wherein the non-optical signal is indicative of a change in ion concentration at one or more of the reaction sites.

6. The method of claim 1, wherein the surface has 100-700 million reaction sites that are in fluid communication with each other.

7. The method of claim 1, wherein the surface has 100-700 million reaction sites.

8. The method of claim 1, wherein each of the reaction sites is attached or operatively linked to at least one isFET or chemFET.

9. The method of claim 5, wherein the change in ion concentration is a change in the concentration of hydrogen ions.

10. The method of claim 1, wherein the first solution contains one type or a mixture of different types of terminator nucleotides.

11. The method of claim 1, wherein the first binding partner comprises biotin or a derivative thereof, digoxigenin, dinitrophenol, bromodeoxyuridine or an antigen.

12. The method of claim 1, wherein the second binding partner comprises a biotin-binding protein, an avidin moiety or a derivative thereof, streptavidin or an antibody.

13. The method of claim 1, wherein the signal-generation moiety comprises a catalytic enzyme capable of converting a substrate into a non-optical detectable signal.

14. The method of claim 13, wherein the non-optical detectable signal is generated upon contacting the catalytic enzyme with a substrate of the enzyme.

15. The method of claim 14, wherein the non-optical signal is indicative of a change in ion concentration.

16. The method of claim 15, wherein the non-optical signal is a pH-based signal.

17. The method of claim 1, wherein the signal-generation moiety comprises a phosphatase or peroxidase.

18. The method of claim 1, wherein the terminator moiety comprises a phosphate group.

19. The method of claim 1, wherein the at least one sensor is an ion sensor.

20. The method of claim 1, wherein each reaction site comprises a reaction chamber having a volume no greater than 1.0 pL, or no greater than 0.34 pL, or no greater than 0.096 pL, or no greater than 0.012 pL.

* * * * *